(12) United States Patent
Lenna et al.

(10) Patent No.: US 11,840,519 B2
(45) Date of Patent: Dec. 12, 2023

(54) PROCESS FOR THE SYNTHESIS OF THE SODIUM SALT OF 4-[[(1R)-2-[5-(2-FLUORO-3-METHOXYPHENYL)-3-[[2-FLUORO-6-(TRIFLUOROMETHYL)-PHENYL]METHYL]-3,6-DIHYDRO-4-METHYL-2,6-DIOXO-1(2H)-PYRIMIDINYL]-1-PHENYLETHYL]AMINO]-BUTANOIC ACID (ELAGOLIX SODIUM SALT) AND INTERMEDIATES OF SAID PROCESS

(71) Applicant: INDUSTRIALE CHIMICA S.R.L., Milan (IT)

(72) Inventors: Roberto Lenna, S. Giorgio su Legnano (IT); Andrea Fasana, Nesso (IT); Jerry Ortiz, Milan (IT)

(73) Assignee: INDUSTRIALE CHIMICA S.R.L., Milan (IT)

( * ) Notice: Subject to any disclaimer, the term of this patent is extended or adjusted under 35 U.S.C. 154(b) by 0 days.

(21) Appl. No.: 17/639,638

(22) PCT Filed: Jul. 27, 2020

(86) PCT No.: PCT/IB2020/057065
§ 371 (c)(1),
(2) Date: Mar. 2, 2022

(87) PCT Pub. No.: WO2021/044230
PCT Pub. Date: Mar. 11, 2021

(65) Prior Publication Data
US 2022/0281829 A1 Sep. 8, 2022

(30) Foreign Application Priority Data

Sep. 3, 2019 (IT) .......................... 102019000015458
Jan. 24, 2020 (IT) .......................... 102020000001390

(51) Int. Cl.
*C07D 239/553* (2006.01)

(52) U.S. Cl.
CPC ................................ *C07D 239/553* (2013.01)

(58) Field of Classification Search
CPC .......................... C07D 239/54; C07D 239/553
See application file for complete search history.

(56) References Cited

FOREIGN PATENT DOCUMENTS

| WO | 2005/007165 A1 | 1/2005 |
| WO | 2017/221144 A1 | 12/2017 |

OTHER PUBLICATIONS

Liu, Rong, ed., Water-Insoluble Drug Formulation (CRC Press, 2008) Chapter 15 pp. 417-435.*
Bastin et al., Organic Process Research & Development 2000, 4, 427-435.*
Morris, et al., International Journal of Pharmaceutics 105 (1994) 209-217.*
Adeyeye, Moji, ed., Preformulation in Solid Dosage Form Development (Informa Healthcare, 2008) Chapter 2.3, pp. 63-80.*
Gould, International J. of Therapeutics 33, 201-213 (1986).*
Swarbrick et al., eds. Encyclopedia of Pharmaceutical Technology 13 (Marcel Dekker, NY 1996) pp. 453-499.*
Serajuddin, Advanced Drug Delivery Reviews 59 (2007) 603-616.*
International Search Report and Written Opinion for corresponding Application No. PCT/IB2020/057065 (dated Sep. 18, 2020).
International Preliminary Report on Patentability for corresponding Application No. PCT/IB2020/057065 (dated Aug. 6, 2021).

* cited by examiner

*Primary Examiner* — Deepak R Rao
(74) *Attorney, Agent, or Firm* — Troutman Pepper Hamilton Sanders LLP (Rochester)

(57) ABSTRACT

The present invention to a process for the preparation of the sodium salt of 4-[[(1R)-2-[5-(2-fluoro-3-methoxyphenyl)-3-[[2-fluoro-6-(trifluoromethyl)phenyl]methyl]-3,6-dihydro-4-methyl-2,6-dioxo-1(2H)-pyrimidinyl]-1-phenylethyl]-amino]-butanoic acid, compound also known as Elagolix sodium salt, having the formula (I) reported below:

(I)

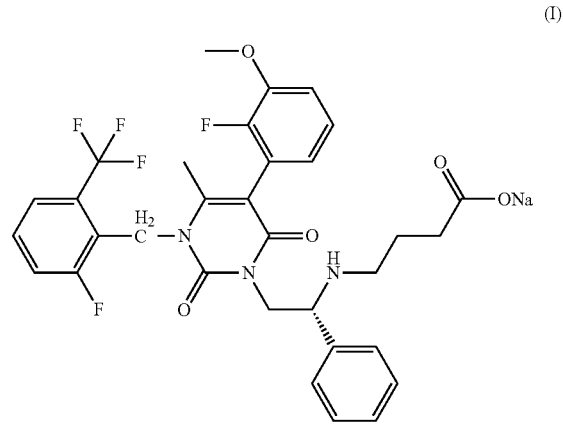

13 Claims, 5 Drawing Sheets

PROCESS FOR THE SYNTHESIS OF THE SODIUM SALT OF 4-[[(1R)-2-[5-(2-FLUORO-3-METHOXYPHENYL)-3-[[2-FLUORO-6-(TRIFLUOROMETHYL)-PHENYL]METHYL]-3,6-DIHYDRO-4-METHYL-2,6-DIOXO-1(2H)-PYRIMIDINYL]-1-PHENYLETHYL]AMINO]-BUTANOIC ACID (ELAGOLIX SODIUM SALT) AND INTERMEDIATES OF SAID PROCESS

This application is a national stage application under 35 U.S.C. § 371 of PCT Application No. PCT/IB32020/057065, filed Jul. 27, 2020, which claims the priority benefit of Italian Patent Application No. 102019000015458, filed Sep. 3, 2019, and Italian Patent Application No. 102020000001390, filed Jan. 24, 2020.

FIELD OF THE INVENTION

The present invention relates to the sector of processes for the synthesis of active ingredients for pharmaceutical use, and in particular to a process for the industrial scale preparation of the sodium salt of 4-[[(1R)-2-[5-(2-fluoro-3-methoxyphenyl)-3-[[2-fluoro-6-(trifluoromethyl)phenyl]methyl]-3,6-dihydro-4-methyl-2,6-dioxo-1(2H)-pyrimidinyl]-1-phenylethyl]amino]-butanoic acid. The invention also relates to some intermediates of the process.

The compound, also known by the name of Elagolix sodium salt, is an active ingredient useful in the treatment of the pain associated with endometriosis in women. It is also in the development phase for the treatment of uterine fibroids and heavy periods in women.

The structural formulae of Elagolix and of its sodium salt are reported below:

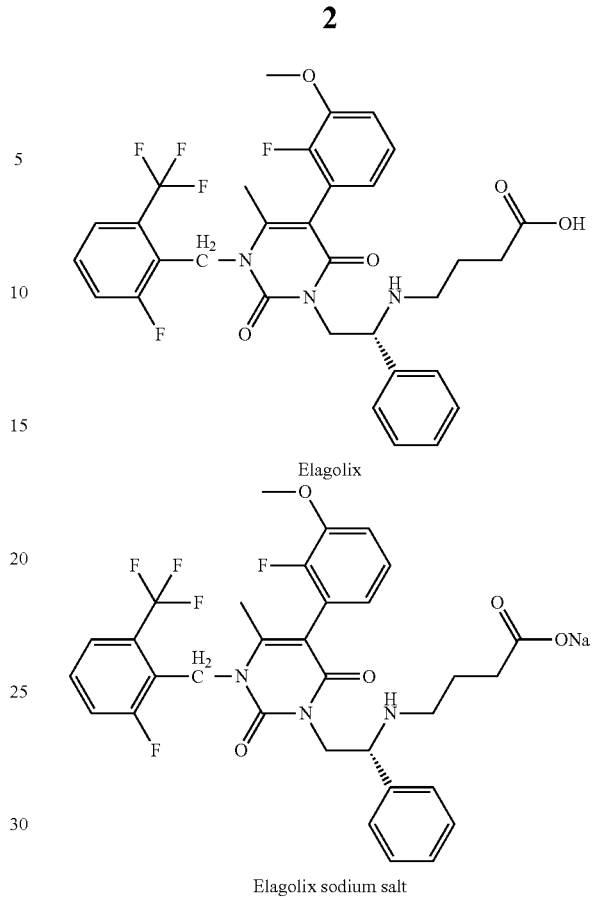

Elagolix

Elagolix sodium salt

BACKGROUND

The sodium salt of Elagolix (hereinafter also indicated as Elagolix sodium salt or "Elagolix sodium") is described and claimed in patent EP 1646389 B1 dated 2006, in the name of Neurocrine Biosciences Inc.

The patent reports a detailed experimental description of the preparation of the target compound. Example 1 of the patent, on pages 14-16, reports a process for the synthesis of the sodium salt of Elagolix starting from 2-fluoro-6-(trifluoromethyl)benzonitrile; the process layout of this patent is reported below as scheme 1:

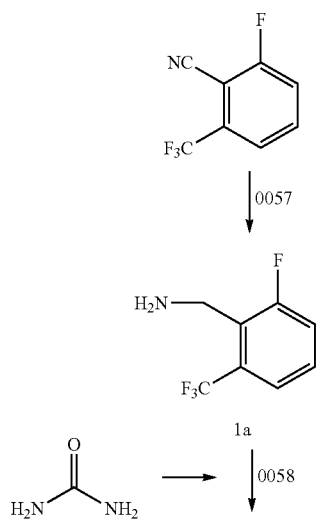

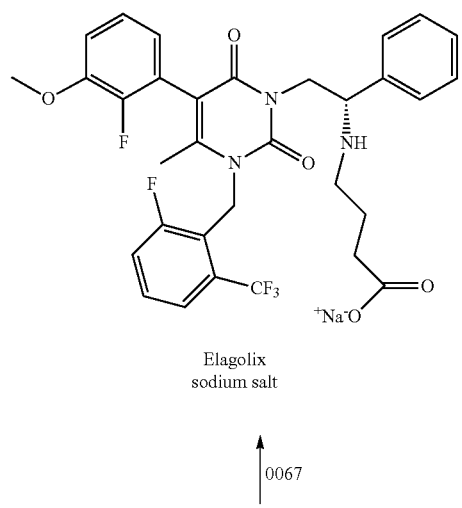

Elagolix sodium salt

-continued
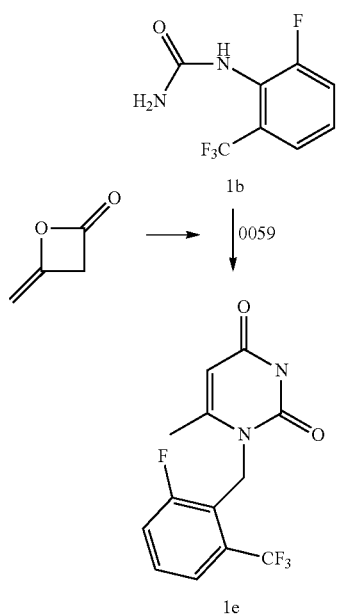
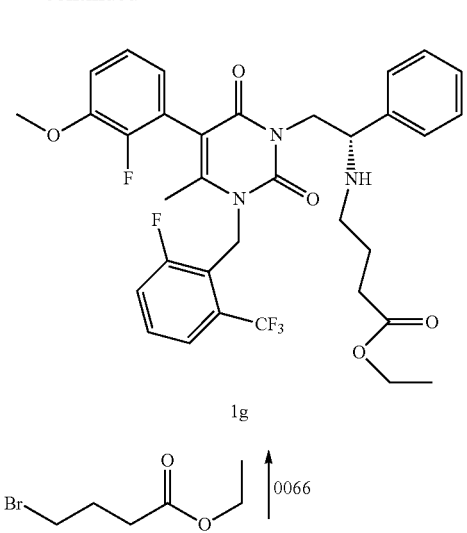
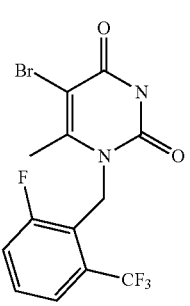
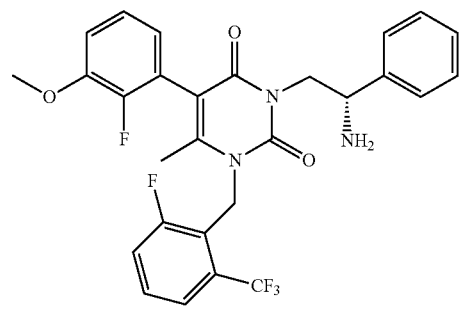
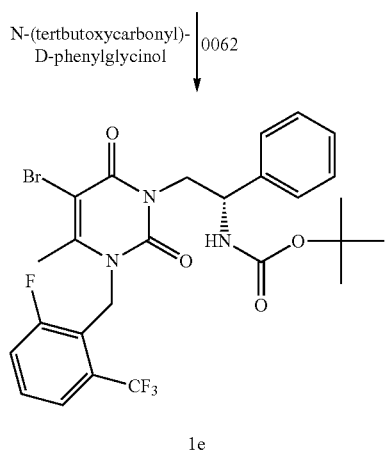
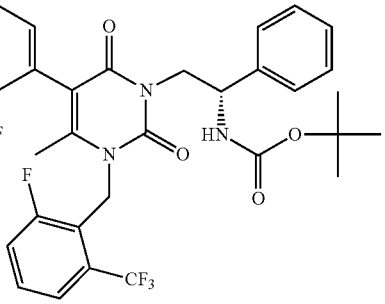
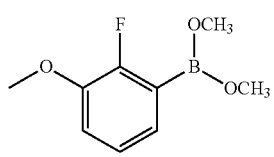

The synthesis steps 1d→1e [0062], 1e→1f [0063], 1f→1g [0066] and 1g→Elagolix sodium salt [0067] all envisage a chromatographic purification. In particular, steps 1d→1 [0062], 1e→1f [0063], 1f→1g [0066] require a preparatory chromatographic operation on silica gel, whereas the final step from 1g→Elagolix sodium salt [0067] requires a chromatography operation on an ion exchange resin.

These purification techniques are not inapplicable a priori to industrial scale production, but require investments, in terms of equipment, performance time, use of organic solvents and analytical commitment for the control of the chromatography fractions which, in fact, exclude the application thereof.

The need is then still felt to have available a new synthesis process of the Elagolix sodium salt that overcomes the drawbacks of the above process.

The aim of the present invention is that of providing a synthesis route for the preparation of the sodium salt of 4-[[(1R)-2-[5-(2-fluoro-3-methoxyphenyl)-3-[[2-fluoro-6-(trifluoromethyl)phenyl]methyl]-3,6-dihydro-4-methyl-2,6-dioxo-1(2H)-pyrimidinyl]-1-phenyl ethyl] amino]-butanoic acid (Elagolix sodium salt), which is industrially applicable and which enables a pharmaceutical quality product to be obtained overcoming the critical issues that accompany the described processes of the prior art.

SUMMARY OF THE INVENTION

This aim is achieved by the present invention which, in a first aspect thereof, relates to a process for the synthesis of the Elagolix sodium salt comprising the following steps:

a) reaction of the compound N-6, 5-bromo-1-[2-fluoro-6-(trifluoromethyl)benzyl]-6-15 methylpyrimidine-2,4(1H,3H)-dione, with D-BOC-phenylglycinol to obtain the intermediate 5-bromo-1-[2-fluoro-6-(trifluoromethyl)benzyl]-6-methyl-3[2(R)-tert-butoxycarbonylamino-2-phenylethyl]-pyrimidine-2,4(1H,3H)-dione (intermediate N-5):

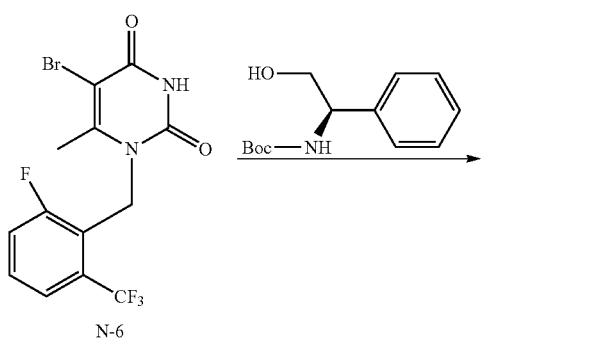

b) treatment of the intermediate N-5 with hydrochloric acid in ethanol to obtain the intermediate 5-bromo-1-[2-fluoro-6-(trifluoromethyl)benzyl]-6-methyl-3[2(R)-amino-2-phenylethyl]-pyrimidine-2,4(1H,3H)-dione hydrochloride (intermediate N-4):

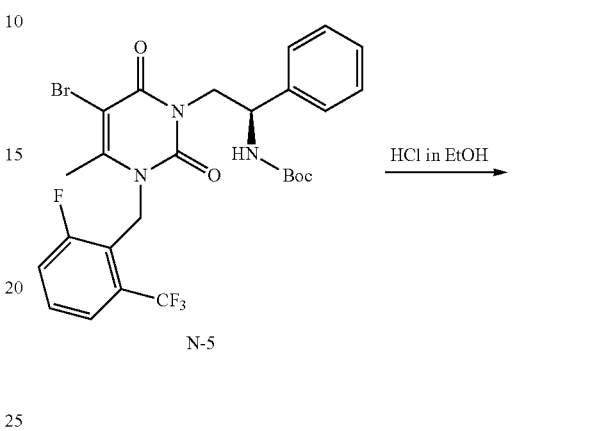

c) treatment with bases of the intermediate N-4 and reaction with ethyl 4-bromobutanoate to obtain the intermediate N-3, 3-[2(R)-{ethoxycarbonylpropylamino}-2-phenylethyl]-5-bromo-1-[2-fluoro-6-(trifluoromethyl)benzyl]-6-methyl-pyrimidine-2,4(1H,3H)-dione:

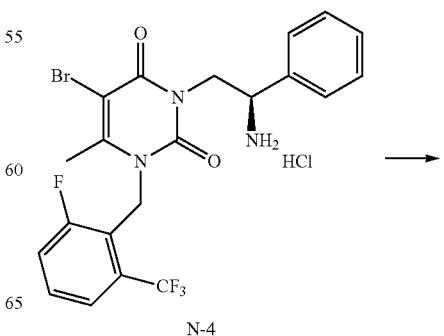

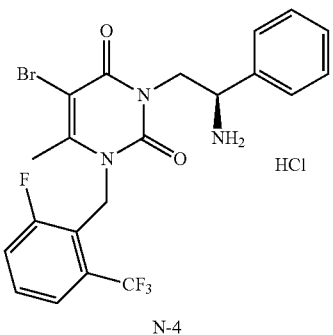

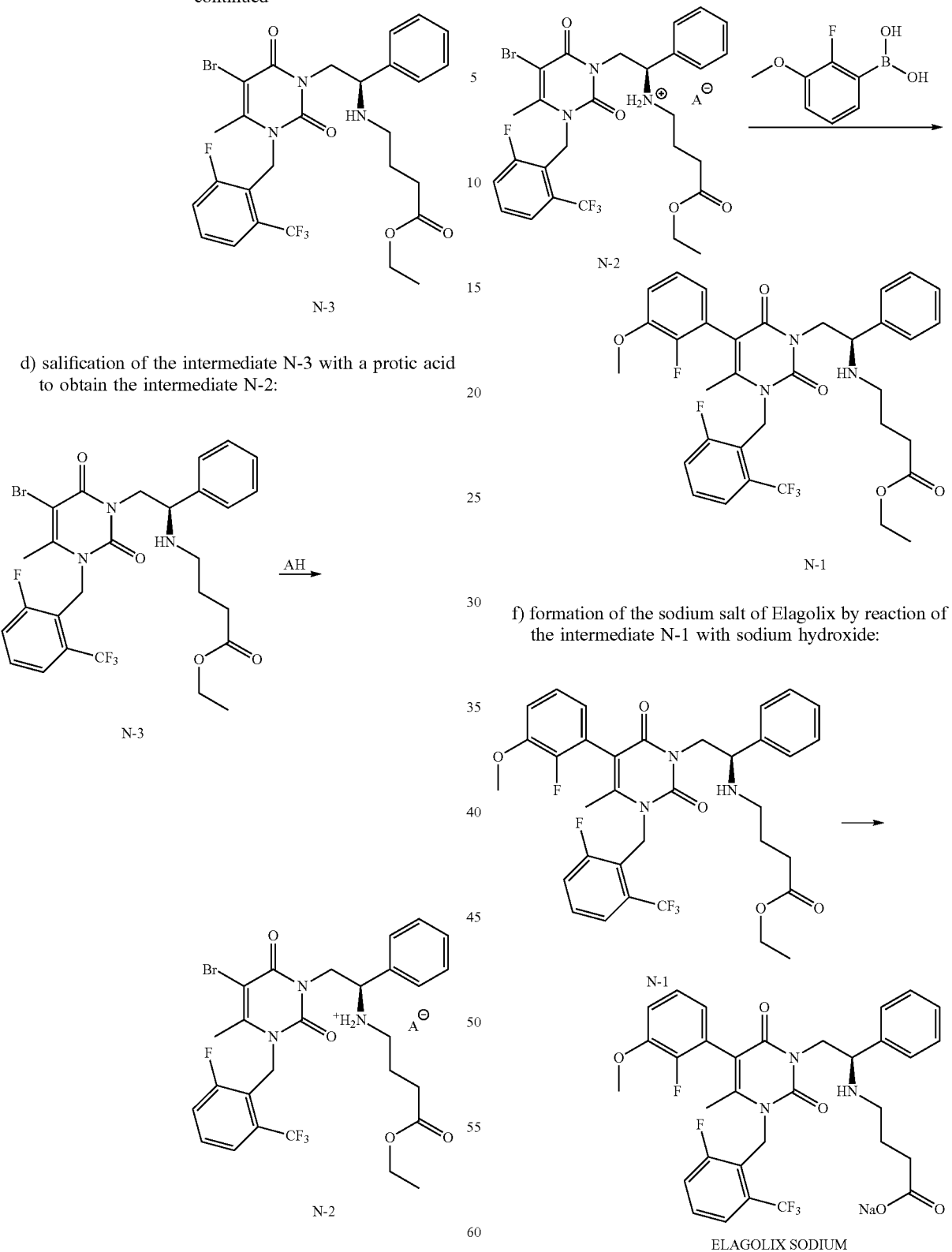

d) salification of the intermediate N-3 with a protic acid to obtain the intermediate N-2:

e) reaction of the intermediate N-2 with 2-fluoro-3-methoxyphenylboronic acid to obtain the intermediate N-1,3-[2(R)-{ethoxycarbonylpropyl-amino}-2-phenyl-ethyl]-5-(2-fluoro-3-methoxyphenyl)-1-[2-fluoro-6-(trifluoromethyl)benzyl]-6-methyl-pyrimidine-2,4(1H, 3H)-dione:

f) formation of the sodium salt of Elagolix by reaction of the intermediate N-1 with sodium hydroxide:

In an alternative embodiment of the process of the invention, in the event in which steps c) and d) are performed in the same solvent, these two steps can be performed as a single step directly obtaining the intermediate N-2 from the intermediate N-4.

In the second aspect thereof, the invention relates to the intermediates N-4, N-3 and N-2 of the process described above.

DETAILED DESCRIPTION OF THE INVENTION

Figure 1:
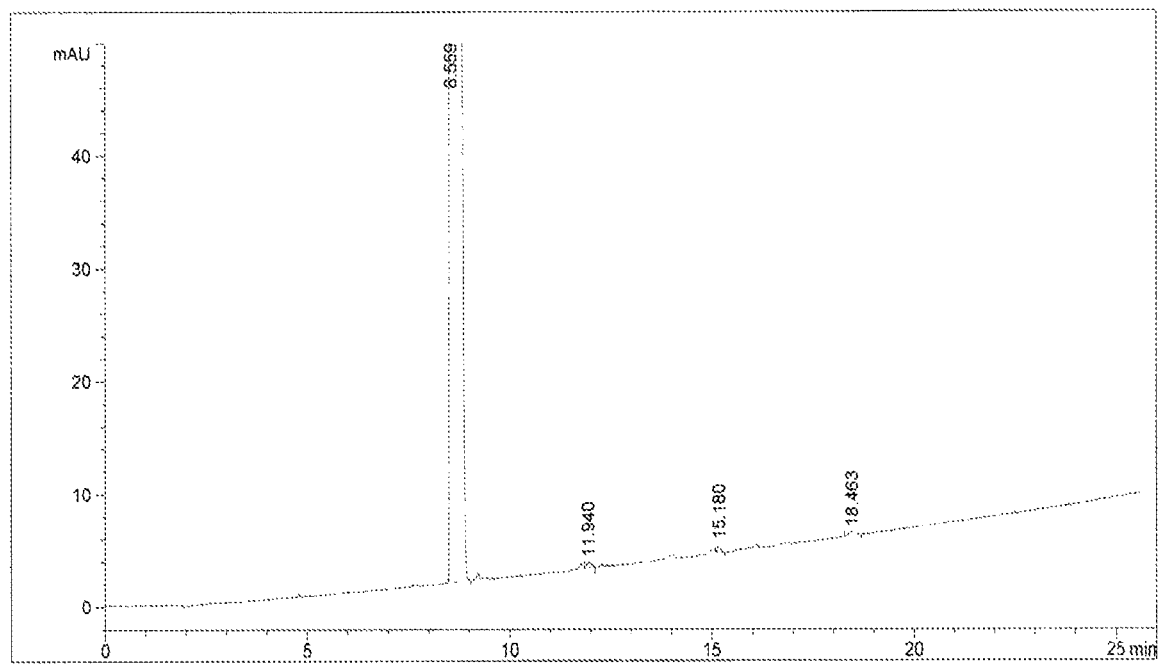
FIG. 1 shows the HPLC chromatogram of the Elagolix sodium salt that can be obtained through the process of the invention.

In the first aspect thereof, the invention relates to a process for the synthesis of the Elagolix sodium salt that requires six synthetic steps.

The first step, a), uses the compound N-6 as a reactant:

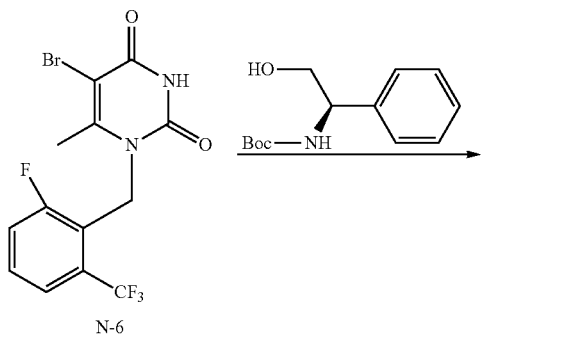

N-6

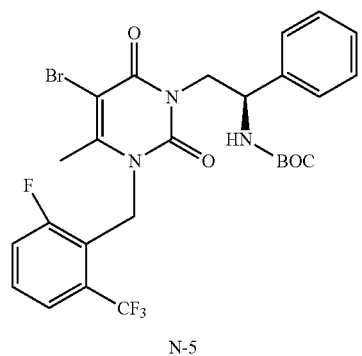

N-5

The starting reactant of this step, compound N-6, can be obtained as described in patent EP 1646389 B1.

The reaction from compound N-6 to intermediate N-5 can also be performed following the indications reported in the cited patent.

Unlike what is described in said patent, however, the intermediate N-5 is not purified by chromatography, but through the treatment of the crude product with an organic ester such as ethyl acetate (AcOEt), butyl acetate (BuOAc) or isopropyl acetate (iPrOAc). The use of isopropyl acetate (iPrOAc) is preferred. Such treatment can be performed at a temperature between 0 and 25° C., preferably between 5 and 15° C.

Step b) consists of the formation of the hydrochloride of the intermediate N-5 (this hydrochloride constitutes the intermediate N-4):

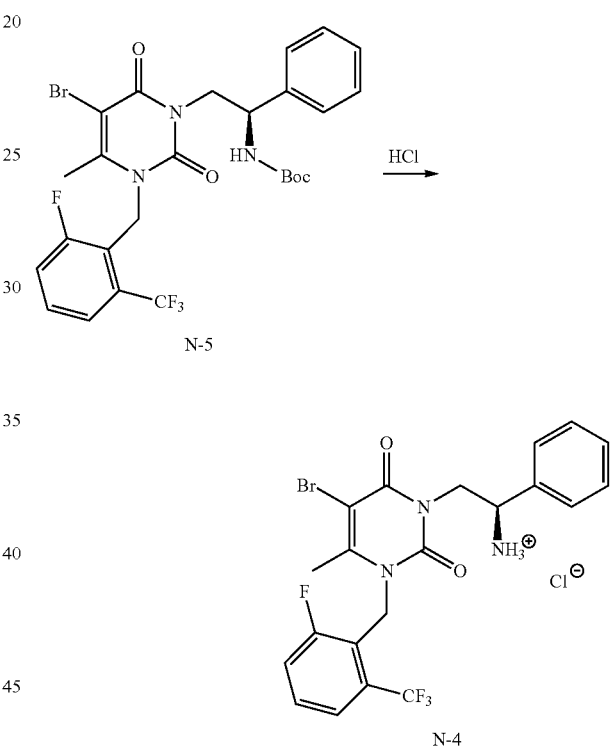

This step can be performed by preparing a solution of the intermediate N-5 in an organic solvent (compatible with the presence of hydrochloric acid) to which the hydrochloric acid is then added. The hydrochloric acid can be introduced into the solution of the intermediate N-5 directly as a gas (e.g. by bubbling), or, preferably, it can be added as an aqueous solution or as a solution previously prepared in the same organic solvent in which the intermediate N-5 was previously dissolved.

The solvents that can be used are ethanol, methanol, isopropanol, acetone, methyl isobutyl ketone (MIBK), ethyl acetate, isopropyl acetate, pure or mixed together. The preferred solvent is ethanol.

The reaction temperature is between 5 and 35° C., preferably between 20 and 30° C. Step c) of the process of the invention consists of the transformation of the intermediate N-4 into the intermediate N-3:

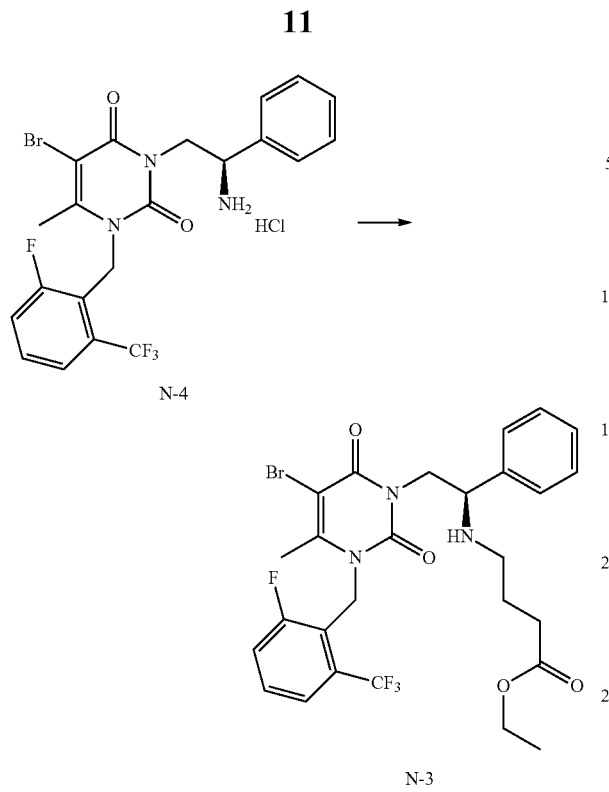

N-4

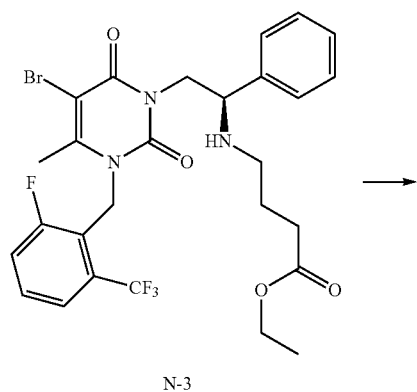

N-3

This step can be performed according to a sequence of two operations, the first of which, c.1, consists in suspending the intermediate hydrochloride N-4 in an organic ester such as ethyl acetate (AcOEt), butyl acetate (BuOAc) or isopropyl acetate (iPrOAc) and treating it with an inorganic base; the second operation, c.2, consists in reacting the amine function released in operation c.1 with the compound ethyl 4-bromo-butanoate. Preferably, the organic ester used in operation c.1 is isopropyl acetate (iPrOAc).

The reaction temperature of operation c.2 is between 30 and 55° C., preferably between 30 and 50° C., and requires a time between 18 and 48 hours.

Higher temperatures lead to an increase in by-products to the detriment of the formation of the reaction product (in this regard see comparative Example 7, performed at T=80° C.).

Step d) consists in the formation of the salt of intermediate N-3 by reaction with a protic acid (the salt constitutes the intermediate N-2):

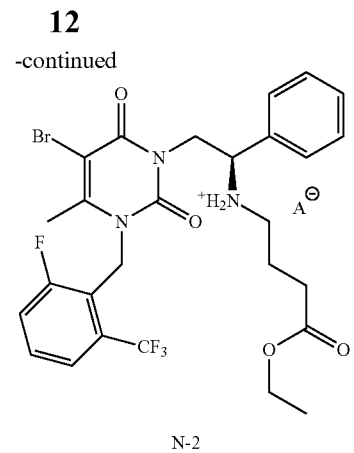

N-2

This step is performed by preparing a solution of the intermediate N-3 in an organic solvent (compatible with the presence of protic acid) to which the protic acid is then added.

The protic acid, although indicated with the general formula AH, is not limited to monoprotic acids able to yield one proton only. This acid can be selected from hydrochloric acid, sulfuric acid, phosphoric acid, hydrobromic acid, p-toluenesulfonic acid or trifluoroacetic acid. Preferably, hydrochloric acid or phosphoric acid $H_3PO_4$ are used.

The acid can be introduced pure into the solution of the intermediate N-3 (e.g. in gaseous form in the case of hydrochloric acid) or, preferably, in form of an aqueous solution.

The organic solvents that can be used for preparing the solution of the intermediate N-3 are ethanol, methanol, isopropanol, acetone, methyl butyl ketone (MIBK), ethyl acetate, isopropyl acetate and butyl acetate, pure or mixed together; the use of isopropyl acetate is preferred. The addition of acid takes place at a temperature between 10 and 35° C., preferably between 20 and 30° C.

The isolation of the intermediate N-2 is obtained by filtration after precipitation of the salt from the organic phase acidified by addition of an antisolvent or by filtration after the precipitation of the salt from the corresponding aqueous phase. As an antisolvent it is possible to use C6 and C7 linear, cyclic or branched hydrocarbons, pure or mixed together; the preferred compound for this purpose is normal-heptane (n-heptane).

In an alternative embodiment of the process, the two steps can be performed as a single step. The two steps are separate if the intermediate N-3 is isolated at the end of step c.2) and then redissolved in the solvent for performing step d); alternatively, if the solvent used in the two steps is the same (e.g. iPrOAc) the acid of step d) can be added directly to the solution of intermediate N-3 obtained at the end of step c.2), as shown in Example 8, passing directly from intermediate N-4 to intermediate N-2.

Step e) of the process consists in adding the radical 2-fluoro-3-methoxyphenyl to the intermediate N-2, with a reaction known as "coupling", to obtain the intermediate N-1:

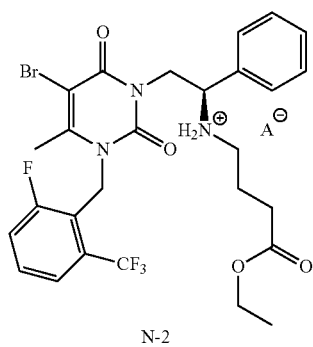

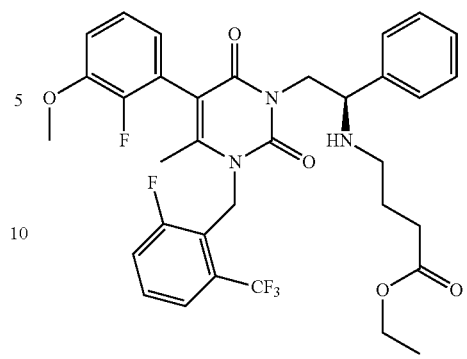

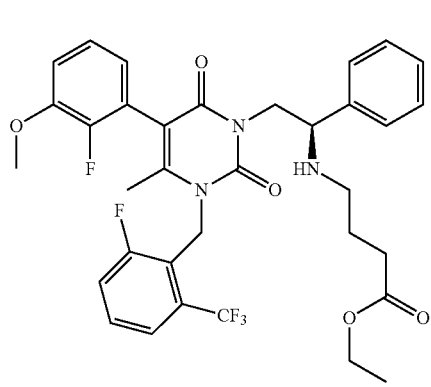

N-1

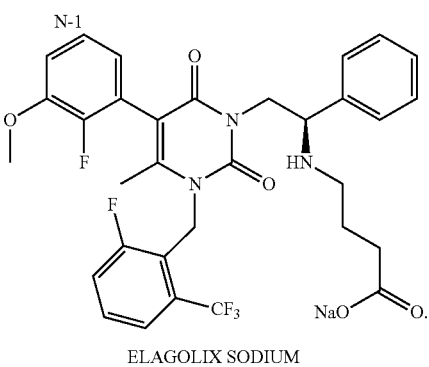

ELAGOLIX SODIUM

This reaction can be performed directly using the intermediate N-2.

The conditions for performing this reaction are described in more detail in examples 5, 9 and 12, and comprise, for example:

reaction in solvent degassed with nitrogen;

the addition of KOH to the solution of the intermediate N-2, followed by heating and subsequent addition of palladium acetate;

reaction at a temperature between 45 and 55° C. for a period between 1 and 24 hours controlling the trend of the reaction with TLC or HPLC.

The conditions listed above do not constitute an exhaustive list for performing the step.

In the event that the reaction is not finished it is possible to add ethanol to the reaction mixture in order to degrade the unreacted intermediate N-2 (see Example 9 on this point).

Finally, the last step of the process of the invention, f), consists in the hydrolysis of the ester group of the intermediate N-1 with sodium hydroxide and the formation of the sodium salt of the acid thus obtained, Elagolix sodium salt:

The hydrolysis of an ester is a well-known reaction in organic chemistry, and the definition of the conditions for the performance thereof is known to a person skilled in the art.

Characterizing features of the invention are in particular steps b), c) and d), which take intermediate N-5 to intermediate N-2.

Further objects of the invention are the intermediates N-4, N-3 and N-2, previously mentioned.

The invention will be further illustrated by the following examples.

Experimental Instruments, Methods and Conditions

NMR: NMR JEOL 400 YH (400 Mhz) spectrometer; JEOL Delta v5.1.1 software; spectra recorded in deuterated solvents such as: chloroform-d, D 99,8%, containing 0.1% (v/v) tetramethylsilane (TMS) as internal standard; and chloroform-d, "100%", D 99,96%, containing 0.03% (v/v) TMS, $CD_3OD$ and DMSO-$d_6$.

TLC: MERCK: TLC silica gel 60 $F_{254}$ Aluminium sheets 20×20 cm, cod. 1.0554.0001.

HPLC: chromatographic system Agilent model 1200 Infinity; Detector UV mod. G1315D DAD. Chromatography conditions:

Column: Zorbax eclipse XDB-C18 150×4.6 mm, 3.5 μm

Flow rate: 1.5 ml/min

Detector: UV 275 nm

Injection volume: 5 μl

Temperature: 20° C.

Mobile phase A: $H_2O$+0.05% trifluoroacetic acid (TFA)

Mobile phase B: acetonitrile+0.05% TFA

| Time (min) | Mobile phase A (v/v) | Mobile phase B (v/v) |
| --- | --- | --- |
| 0 | 70 | 30 |
| 0-24 | 10 | 90 |
| 24-26 | 2.5 | 97.5 |
| 26-26.2 | 70 | 30 |
| 26.2-35 | 70 | 30 |

Chiral HPLC: chromatographic system Agilent model 1200 Infinity; Detector UV mod. G1315D DAD. Chromatography conditions:
  Column: ASTEC CHIROBIOTIC T (Supelco) 25×4.6 mm, 5 µm
  Flow rate: 1 ml/min
  Detector: UV 275 nm
  Injection volume: 5 µl
  Temperature: 25° C.
  Mobile phase A: 95% by volume, methanol brought to pH=4 with acetic acid
  Mobile phase B: 5% by volume, buffer solution with ammonium acetate-acetic acid at pH=4.

LC/Ms/Ms system: Agilent chromatography system model 1100 with UV DAD detector connected to an API 2000 mass spectrometer by Applied Biosystem.

HPTLC: MERCK: HPTLC silica gel 60 $F_{254}$ with concentration zone 10×2.5 cm, cod. 1.13727.0001.

TLC detectors: potassium permanganate solution. Preparation: 9 g of potassium permanganate, 60 g of potassium carbonate and 900 mL of water are shaken until dissolution with 15 mL of 5% sodium hydroxide solution; the plate is then impregnated with the solution then heated until the products are detected.

The DSC analysis was performed using a Perkin Elmer Diamond differential scanning calorimeter. The samples were encapsulated in aluminium crucibles prior to analysis. The heating of the sample and of the reference was performed at a speed of 10° C./min in the temperature range 25-180° C. The thermogram was analysed using Pyris Data Analysis 8 Perkin Elmer software.

The DRX diffractometry analysis was performed using a Bruker D2 Phaser ($2^{nd}$ ed.) diffractometer operating in Bragg-Brentano geometry and equipped with a rotating 6-position multisampler. The X-ray source used is a tube with a copper anode operated at 30 kV and 10 mA. The analytical wavelength selected is the Kα of copper (λ=1.54184 Å) obtained by filtering Kβ using a nickel filter. The X-ray detector used is a solid state linear detector model LYNXEYE. For the analysis the samples were deposited on a flat single-crystal silicon sample holder plate of the zero background type. The sample was rotated during analysis at a speed of 60 rotations/min. The analysis was performed in the range 4-40° 2θ with 0.016° increases and an acquisition time of 1.0 s for each increase. The display and processing of the diffractogram were performed using Diffrac.EVA (Bruker) software.

The FTIR spectra were acquired using a Thermo Nicolet 6700 spectrophotometer equipped with an ATR accessory, model Smart iTR. 64 read-only scans were performed both for the sample and for the background, using a resolution of 4 $cm^{-1}$, acquiring the background immediately before the sample. The display and processing of the FTIR spectrum were performed using Omnic (Thermo Nicolet) software.

The water used for performing the experimental tests is to be considered pure unless otherwise indicated.

The organic solvents used in the tests are to be considered "technical" grade unless otherwise indicated.

The reactants and catalysts used in the tests are to be considered commercial grade unless otherwise indicated.

EXAMPLE 1

This example relates to step a) of the process of the invention, from compound N-6 to intermediate N-5.

29.95 g of intermediate N-6, 26.86 g of D-BOC-phenylglycinol, 30.92 g of triphenylphosphine and 299 mL of tetrahydrofuran are loaded in that order into a round-bottom flask. It is cooled to 5° C. and a solution of di-tert-butyl azodicarboxylate (27.19 g) dissolved in 150 mL of tetrahydrofuran is dripped in about 40 minutes. The system is brought to 25° C. and kept in agitation for 1.5 hours.

At the end of the reaction (HPLC control) the solvent is removed by distillation at reduced pressure at 45° C. The residue is added with 377 mL of isopropyl acetate and kept in agitation at 5-10° C. for 1 hour. The suspension is filtered by washing the solid with 20 mL of isopropyl acetate.

The liquid phase obtained by filtration is concentrated at reduced pressure at 45° C. until a yellow oil is obtained that is reacted as such in the subsequent reaction.

The compound N-6, used as a starting reactant of the method, has the appearance of a white solid; its purity, determined with HPLC, is 99%.

$^1$H-NMR (400 MHz, DMSO-$d_6$): δ11.91 (s, 1H); 7.66 (d, 1H, J=7.6 Hz); 7.59-7.51 (m, 2H); 5.34 (s, 2H); 2.46 (s, 3H);

A sample of the intermediate N-5 obtained in the test of the example, purified exclusively for analytical purposes, is analysed and identified through $^1$H-NMR and mass spectroscopy.

$^1$H-NMR (400MHz, DMSO-$d_6$): 7.66 (d, 1H, J=7.6 Hz); 7.61-7.48 (m, 2H); 7.36-7.21 (m, 5H); 5.35 (dd, 2H, J=22,0/17.0 Hz); 4.93-4.88 (m, 1H); 4.10-3.99 (m, 2H); 2.53 (s, 3H); 1.35 (s, 9H).

EXAMPLE 2

This example relates to step b) of the process of the invention.

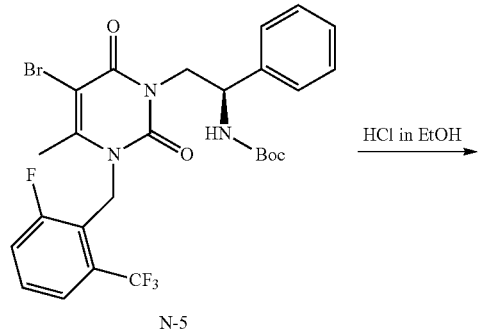

N-5

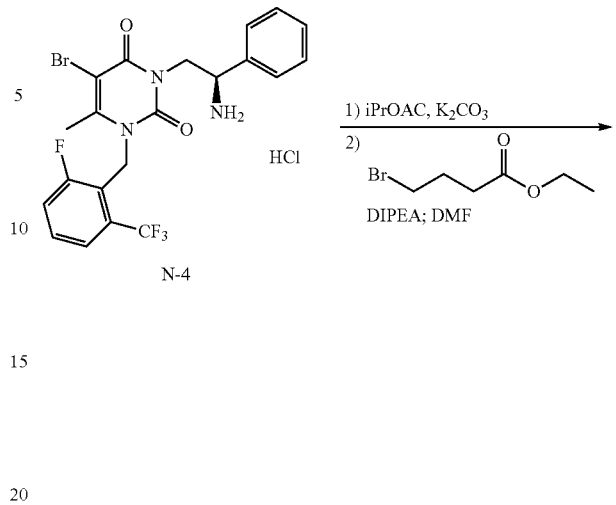

N-4

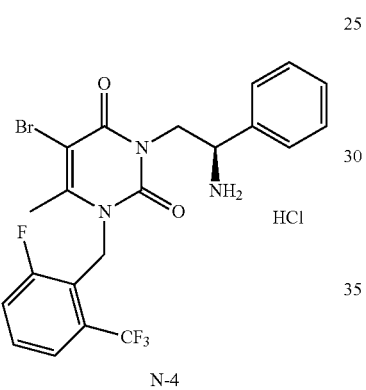

N-4

The intermediate N-5 obtained in the previous example and 120 mL of ethanol are loaded into a round-bottom flask. It is kept in agitation at room temperature for 10 minutes. 50 mL of HCl at 34% in ethanol (concentration by weight) are dripped slowly and kept in agitation at 25° C. for 22 hours.

The reaction is controlled using TLC analysis.

The solid is filtered by washing with 20 mL of ethanol and dried at 60° C. at reduced pressure for 1 hour. 58.53 g of product in white solid form are obtained.

The solid obtained is suspended in 322 mL of methanol and heated to reflux for 30 minutes. It is cooled to 25° C. for 2 hours then to 0° C. for 1 hour. The solid is filtered by washing with 20 mL of cold methanol and dried at reduced pressure and at 60° C. until constant weight.

34.4 g of intermediate N-4 are obtained (white solid, purity HPLC 99.7%).

$^1$H-NMR (400 MHz, DMSO-$d_6$): δ8.85 (br s, 2H); 7.66 (d, 1H, J=7.6 Hz); 7.60-7.53 (m, 2H); 7.39-7.34 (m, 5H); 5.32 (dd, 2H, J=24.0/17.0 Hz); 4.49-4.47 (m, 1H); 4.29-4.26 (m, 2H); 2.55 (s, 3H).

EXAMPLE 3

This example relates to the performance of step c) of the process of the invention.

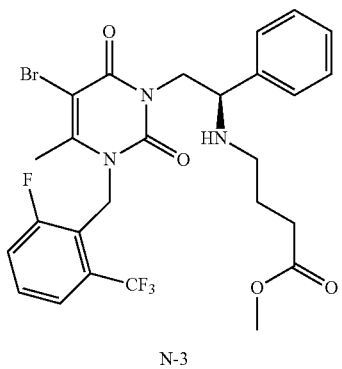

N-3

5 g of intermediate N-4 are suspended in 23.5 mL of isopropyl acetate in a round-bottom flask.

The potassium carbonate solution (8.68 g) in water (33.5 mL) is added and kept under vigorous agitation at 25° C. for 2 hours.

The phases are separated, the organic phase is washed twice with water and 5 mL of N,N-dimethylformamide are added.

The isopropyl acetate is removed at reduced pressure at 45° C. and 2.0 mL of ethyl 4-bromo-butanoate and 2.9 mL of N,N-diisopropylethylamine are added to the solution. The solution is kept in agitation at 35° C. for 40 hours.

At the end of the reaction (the reaction is controlled using HPLC analysis) it is cooled to 25° C. and 25 mL of water and 25 mL of isopropyl acetate are added.

The phases are separated, the organic phase is washed with water and it is concentrated at reduced pressure at 45° C. until reaching a constant weight. 5.6 g of yellow oil (HPLC purity 94.2%) are obtained.

The intermediate N-3 thus obtained is used as such in the reaction of the following example.

EXAMPLE 4

This example relates to the performance of step d) of the process of the invention in which the protic acid is hydrochloric acid.

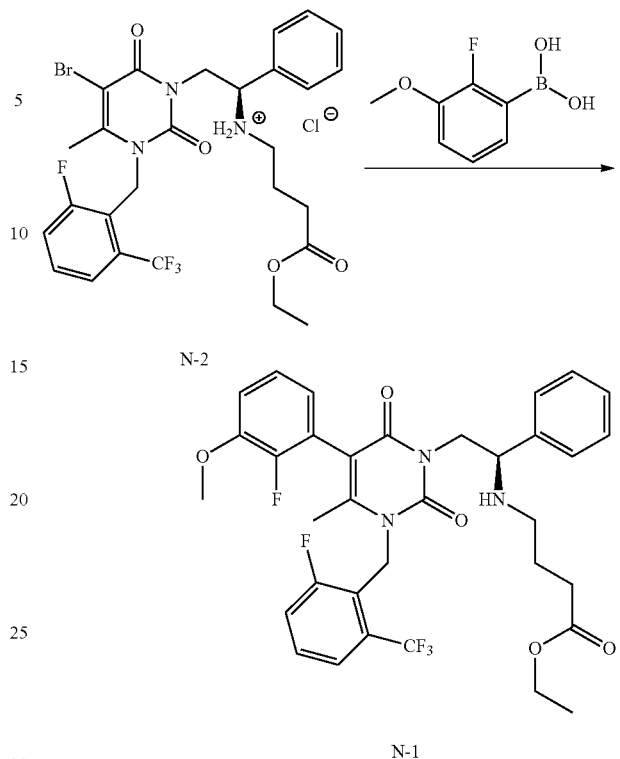

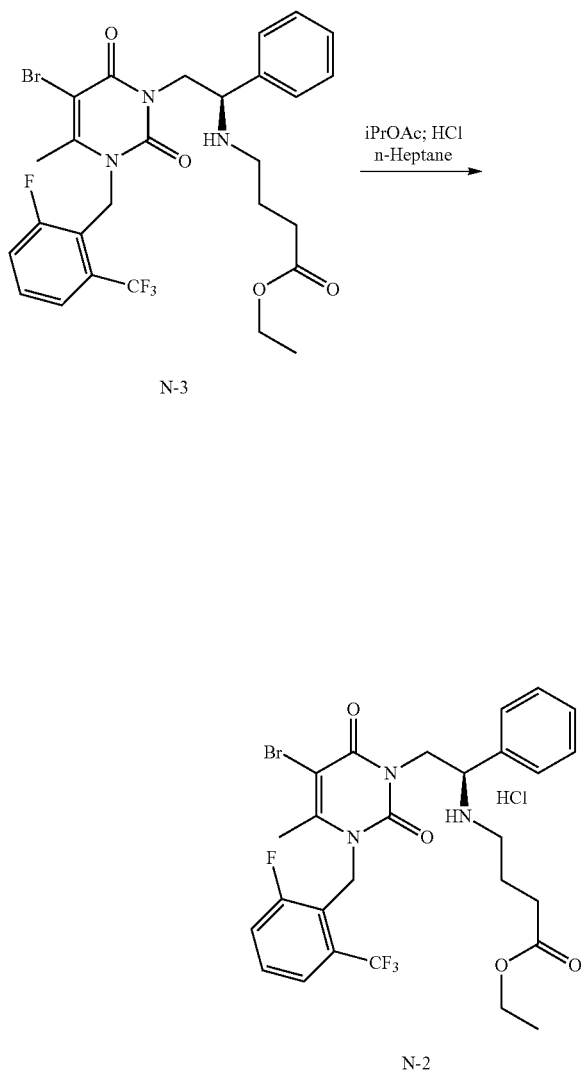

The intermediate N-3, obtained as described in the previous example, is added with 130 mL of isopropyl acetate to which 1 mL of 37% hydrochloric acid is added, keeping the temperature at 25° C. The system is kept in agitation and about 90 mL of solvent are distilled at reduced pressure. Another 20 mL of isopropyl acetate are added and it is concentrated again until a residual volume of about 42 mL. The solution is slowly dripped onto 60 mL of n-heptane cooled to 5° C. It is kept in agitation at 25° C. for 3 hours and the solid is filtered by washing with 40 mL of n-heptane. It is dried at reduced pressure and at 45° C. until reaching a constant weight.

5.1 g of white solid (HPLC purity 91.8%) are obtained.

$^1$H-NMR (400 MHz, DMSO-$d_6$): $\delta$9.75-9-43 (m, 2H); 7.64 (d, 1H, J=7.4 Hz); 7.58-7.50 (m, 2H); 7.39-7.31 (m, 5H); 5.27 (t, 2H, J=17.8 Hz); 4.53-4.50 (m, 2H); 4.36-4.29 (m, 1H); 4.01 (dd, 2H, J=14.2/7.3 Hz); 2.50 (s, 3H); 2.34-2.30 (m, 2H); 1.95-1.80 (m, 2H); 1.30-1.16 (m, 2H); 1.12 (t, 3H, J=7.3 Hz).

EXAMPLE 5

This example relates to the performance of step e) of the process of the invention in which the intermediate N-2 is salified as a hydrochloride.

5 g of intermediate N-2, 3.27 g of 2-fluoro-3-methoxyphenylboronic acid and 60 mL of acetone previously degassed with nitrogen are loaded into a round-bottom flask. The system is cooled to 15° C. and a solution of potassium hydroxide (1.62 g) dissolved in water (30 mL) is added. It is brought to 25° C. and the reaction mixture is degassed for about 10 minutes. 0.45 g of tri-tert-butylphosphonium tetrafluoroborate are added and heated to 45° C. After reaching this temperature 0.17 g of palladium acetate are added and it is heated to 50° C. for one hour.

The reaction is controlled using HPLC analysis. At the end of the reaction it is cooled to 25° C., 25 mL of water and 25 mL of isopropyl acetate are added.

It is filtered on dicalite, the phases are separated, the organic phase is washed with water and it is concentrated at reduced pressure at 45° C. until reaching a residual volume of 24 mL.

The reaction product, dissolved in isopropyl acetate, is extracted with a solution of 85% orthophosphoric acid (3.25 g) in water (30 mL).

The aqueous phase, containing the product, is first washed with 5 mL of isopropyl acetate and then treated with a solution of potassium carbonate (5.75 g) in water (7.3 mL) and finally extracted with 50 mL of isopropyl acetate. The product passes into the organic solution.

The organic phase, washed with water, is concentrated at reduced pressure at 45° C. until it becomes yellow oil (crude intermediate N-1).

The oil, dissolved in methylene chloride, is filtered on silica gel (25 g) washed with 730 mL of a mixture of methyl chloride/isopropyl acetate 80:20.

The solvent is concentrated at reduced pressure and T=45° C. obtaining 3.9 g of colourless oil (HPLC purity 98.8%).

$^1$H-NMR (400 MHz, DMSO-$d_6$): 7.66 (d, 1H, J=7,6 Hz); 7.58-7.51 (m, 2H); 7.24-7.16 (m, 7H); 6.73-6.58 (m, 1H);

5.33 (m, 2H); 4.89-4.82 (m, 1H); 4.00 (dd, 2H, J=14.2/6.8 Hz); 4.03-3.84 (m, 2H); 3.85 (s, 3H); 2.34-2.15 (m, 4H); 2.09 (d, 3H, J=2.7 Hz); 1.53-1.51 (m, 2H); 1.13 (t, 3H, J=7.3 Hz).

EXAMPLE 6

This example relates to step f) of the process of the invention, obtainment of the Elagolix sodium salt.

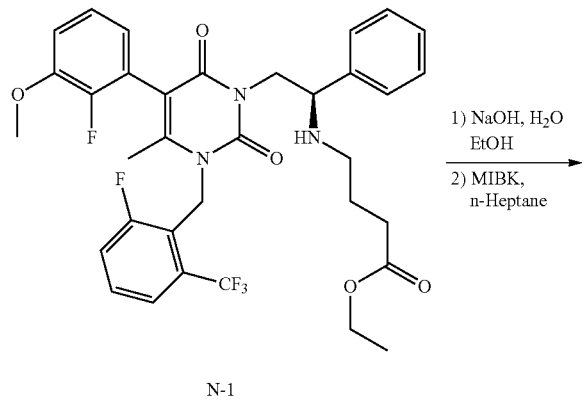

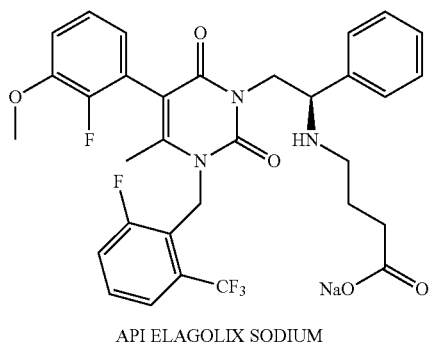

API ELAGOLIX SODIUM 1.84 g of intermediate N-1 and 10 mL of ethanol are loaded into a round-bottom flask. A solution of sodium hydroxide (0.234 g in 7.36 of water) is dripped slowly and the system is heated to 35° C. for 1.5 hours.

The reaction is controlled using TLC analysis.

At the end of the reaction it is cooled to 25° C. and the mixture is concentrated at reduced pressure.

14 mL of water and 14 mL of methyl isobutyl ketone are added to the residue, it is heated to 55° C. for 10 minutes and the phases are separated. The aqueous phase is treated with 4.6 mL of 30% sodium hydroxide and re-extracted twice with 14 mL of methyl isobutyl ketone. The organic phase is washed with 20 mL of saturated sodium chloride solution and concentrated at reduced pressure until obtaining a yellow oil. The residue is added with 15 mL of methyl isobutyl ketone and the solution is filtered on a Millipore filter (0.22 μm). It is concentrated at reduced pressure until reaching a residual volume of 6 mL and dripped slowly into an n-heptane solution (18.4 mL) placed under vigorous agitation and at 25° C. It is kept in agitation for 1 hour and the solid is filtered by washing with n-heptane (4 mL).

It is dried at reduced pressure at 45° C. for 1 hour.

1.3 g of white solid, Elagolix sodium salt of HPLC purity =99.0%, are obtained.

0.840 g of crude Elagolix sodium salt are dissolved in 4 volumes of methyl isobutyl ketone (3.36 mL) and dripped slowly into 10 volumes of n-heptane (8.4 mL) placed under vigorous agitation at 25° C. It is kept in agitation for 1 hour, the solid is filtered by washing with n-heptane and it is dried at reduced pressure at 45° C. for 30 minutes. The same operation is performed three times obtaining 0.550 g of Elagolix sodium salt as a white solid (HPLC purity=99.6%; HPLC titre=99.6%) the $^1$H-NMR and MS analytical data of which coincide with those reported in literature. FIG. 1 shows the significant part of the HPLC chromatogram obtained on a product sample with the experimental set up and in the conditions described above.

Figure 3:
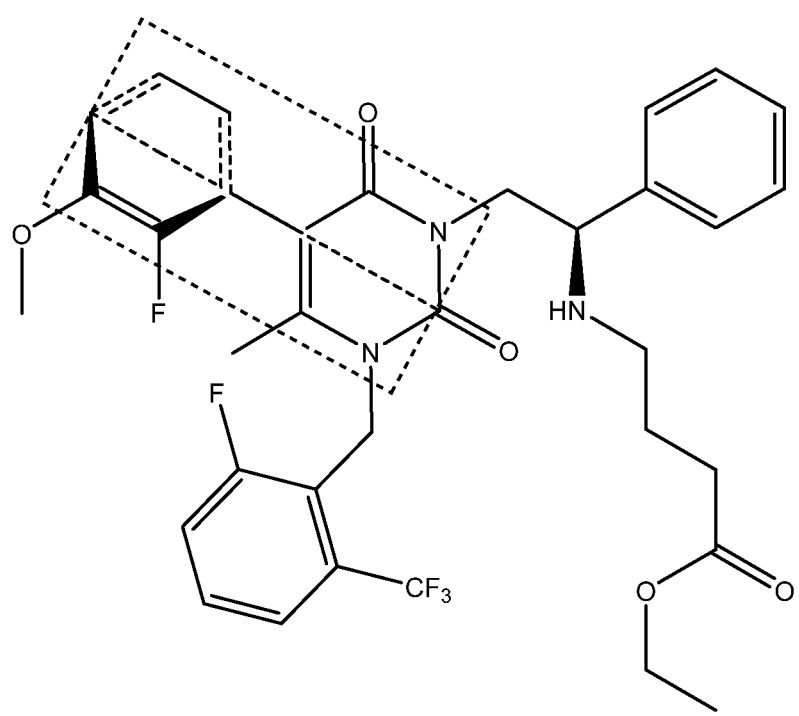
FIG. 3 shows two conformational isomers of Elagolix obtained in a mixture in the process of the invention.
Figure 3:
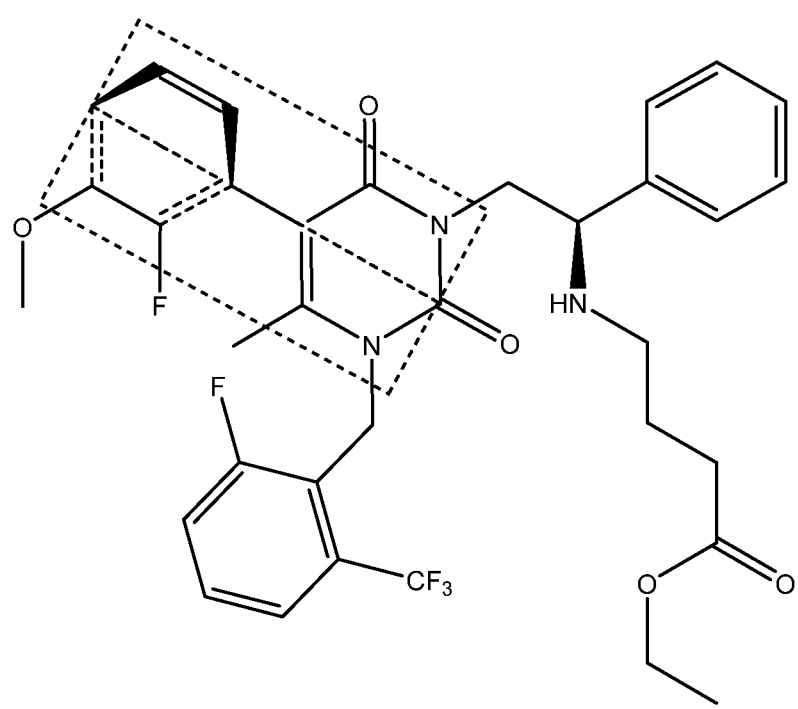

The inventors have also noted that the product is comprised of a mixture of atropic isomers, i.e. conformational isomers the existence of which is due to the steric hindrance of the substituents present on the central ring in the Elagolix molecule (3,6-dihydro-4-methyl-2,6-dioxo-1(2H)-pyrimidinyl radical) and on the 2-fluoro-3-methoxyphenyl radical attached to said central ring. This steric hindrance prevents the free rotation about the bond that unites these two rings, as shown in FIG. 3: in the figure, the rectangles shown in broken lines represent the median plane of the 3,6-dihydro-4-methyl-2,6-dioxo-1(2H)-pyrimidinyl ring, and in the first of the two atropic isomers (shown in the top part of the figure) the 2-fluoro-3-methoxyphenyl group has the fluoro and methoxy phenyl substituents above said plane, while in the second (shown in the bottom part of the figure) said substituents are below the plane.

Figure 2:
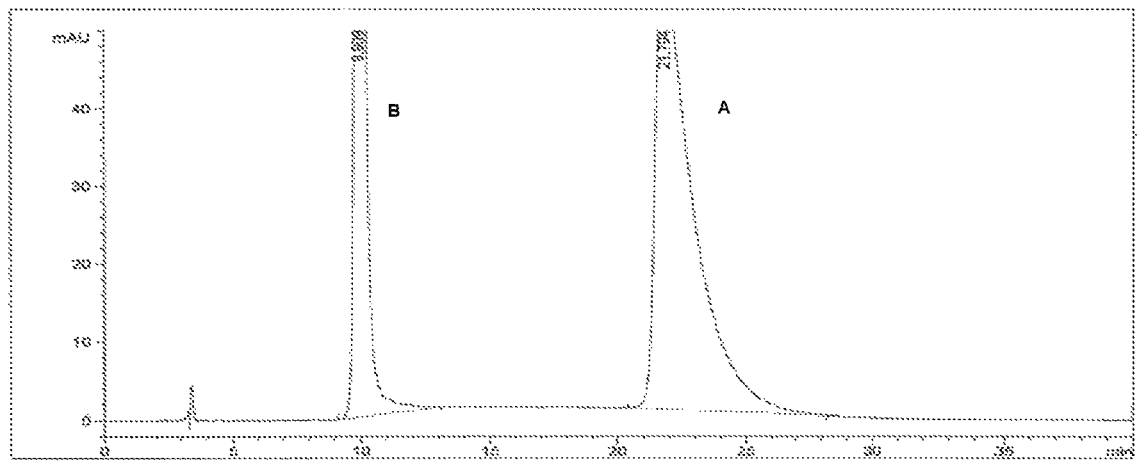
FIG. 2 shows the HPLC chromatogram obtained using a chiral column of the Elagolix sodium salt that can be obtained through the process of the invention.

On a sample of the product obtained in this Example, a HPLC test was then performed on a chiral column, with the experimental set up and in the conditions described above. The chromatogram is reproduced in FIG. 2, which reports the presence of two peaks due to the two atropic isomers separated by the chiral column.

The ratio between the other atropic isomers, determined via chiral HPLC is equal to 1.03.

COMPARATIVE EXAMPLE 7

This example relates to step c) performed at a higher temperature with respect to the conditions of this step according to the invention (80° C. instead of 35° C.).

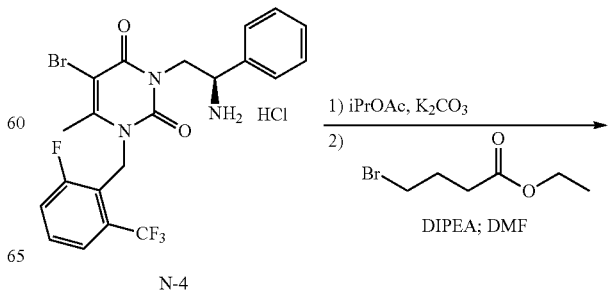

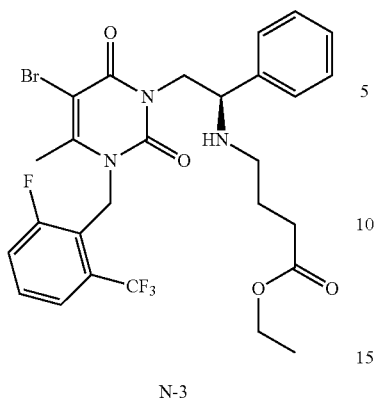

N-3

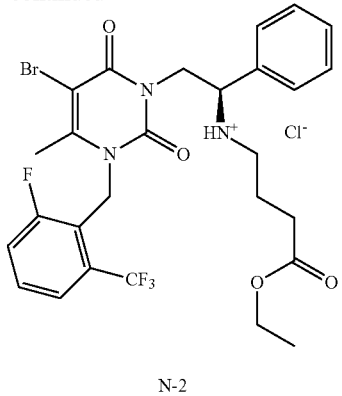

N-2

30 g of intermediate N-4 are suspended in 140 mL of isopropyl acetate in a round-bottom flask.

The solution of potassium carbonate (52 g) in water (200 mL) is added and kept under vigorous agitation at 25° C. for 2 hours.

The phases are separated, the organic phase is washed twice with water and 30 mL of N,N-dimethylformamide are added.

The isopropyl acetate is removed at reduced pressure at 45° C. and 10 mL of ethyl 4-bromo-butanoate and 13.60 mL of N,N-diisopropylethylamine are added to the solution.

The solution is kept in agitation at 80° C. for 20 hours.

At the end of the reaction (the reaction is controlled using HPLC analysis) it is cooled to 25° C. and 150 mL of water and 150 mL of isopropyl acetate are added.

The phases are separated, the organic phase is washed with water and it is concentrated at reduced pressure at 45° C. until reaching a constant weight.

33.6 g of yellow oil (HPLC purity 59%, main impurity 4%) are obtained.

EXAMPLE 8

This example relates to steps c) and d) of the process of the invention performed as a single synthetic step that leads from intermediate N-4 to intermediate N-2 salified as a hydrochloride.

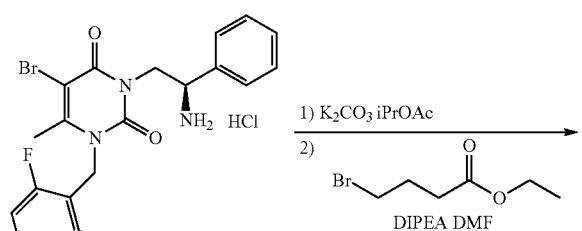

N-4

1) K$_2$CO$_3$ iPrOAc
2)
Br~~~COOEt
DIPEA DMF
3) HCl 37%; iPrOAc; n-Eptano

The intermediate N-4 (57.2 g) and isopropyl acetate (268.7 mL) are loaded into a round-bottom flask under nitrogen. The suspension is kept in agitation (T=25° C. for 10 minutes) after which a solution prepared with potassium carbonate (99.4 g) and water (383 mL) is added to the suspension, keeping the temperature below 25° C. It is kept under vigorous agitation at 25° C. for 12 hours.

The phases are separated, the organic phase is washed with water and N,N-dimethylformamide (138 mL) is added.

The residual isopropyl acetate is removed by distillation at reduced pressure at 45° C.

Ethyl 4-bromo-butanoate (30.5 mL) and N,N-diisopropylethylamine (44.5 mL) are added to the solution, keeping the temperature below 25° C.

The solution is heated to 35° C. and kept under agitation at 35° C. for 40 hours (at the end of the period a HPLC control is performed).

It is cooled to 25° C., 286 mL of water and 286 mL of isopropyl acetate are added.

The phases are separated and the organic phase is washed with water.

Isopropyl acetate (550 mL) is added to the organic phase, the solution is cooled to 15° C. and 37% hydrochloric acid (10.0 mL) is added, keeping the temperature around 25° C. (pH=1).

The solution is concentrated by distillation at reduced pressure then isopropyl acetate (165 mL) and ethanol (5.8 ml) are added and it is agitated for some minutes.

Such solution is dripped onto n-heptane (705 mL) precooled to 5° C. (a white solid precipitates).

The suspension is kept in agitation at 0° C. for 1 hour then the solid is filtered and dried at reduced pressure at 45° C. until reaching a constant weight.

Intermediate N-2=54.5 g (white solid, HPLC purity 92.1%).

EXAMPLE 9

This example relates to step e) of the process of the invention in which the intermediate N-2 is salified as a hydrochloride.

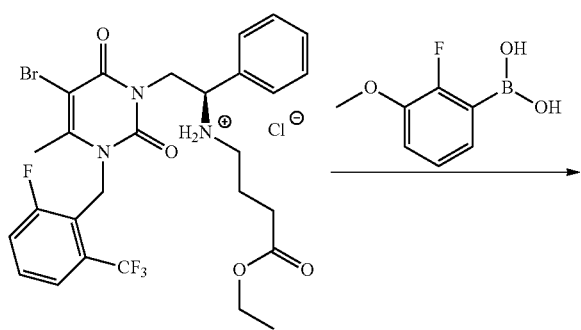

N-2

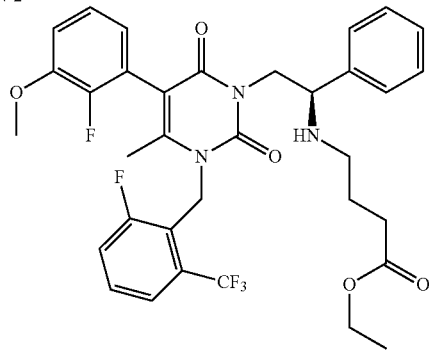

N-1

The intermediate N-2 (13.9 g), 2-fluoro-3-methoxyphenylboronic acid (9.56 g) and tri-t-butyl phosphonium tetrafluoroborate (1.24 g) are loaded into a round-bottom flask under nitrogen.

Acetone (166.8 mL) previously degassed with nitrogen is added and kept in agitation at 25° C. for 10 minutes by bubbling nitrogen into the solution.

The reaction mixture is cooled to 5° C. to which a solution of potassium hydroxide (5.52 g) in water (55.6 mL) degassed with nitrogen is added, keeping the temperature below 15° C. (pH=9).

It is heated to 40° C. while agitating for 1 hour, still bubbling nitrogen into the solution.

It is heated to 50° C., palladium acetate (0.48 g) is added and it is kept under agitation for 16 hours under a nitrogen atmosphere (HPLC control, intermediate N-2 less than 0.2%).

As the HPLC control detected the incomplete disappearance of the intermediate N-2, ethanol (27.8 mL) is added and the agitation continues for 3 hours (HPLC control, intermediate N-2 not detectable).

It is cooled to 25° C.

Water (70 mL) and isopropyl acetate (70 mL) are added.

The two-phase system obtained is filtered and the phases are separated washing the organic phase with water.

The organic phase is concentrated at reduced pressure at 40° C. until reaching a volume of about 120 mL, which is added to an acidic solution obtained by mixing 85% orthophosphoric acid (10.6 g) with water (100 mL).

The two-phase system obtained is kept under agitation at 25° C. for 30 minutes.

The phases are separated: the product is in the aqueous phase, which is washed with isopropyl acetate.

The phases are separated and the aqueous phase (which contains the product) is dripped onto a basic solution obtained with potassium carbonate (18.83 g) and water (24 mL), keeping the temperature at 25-30° C.

Isopropyl acetate (163 mL) is added and the two-phase system is agitated at 25° C. for 20 minutes.

The phases are separated; at this stage of the process, the product is contained in the organic phase, which is washed with water (74 mL).

The organic phase is concentrated at reduced pressure at 45° C. until obtaining an oil that is filtered on a layer of silica gel (67.45 g) with the mixture methylene chloride/isopropyl acetate 80:20.

The solution is concentrated at reduced pressure at 45° C. obtaining 11.0 g of intermediate N-1 (colourless oil, HPLC purity 99%).

EXAMPLE 10

This example relates to the performance of step c) of the process of the invention.

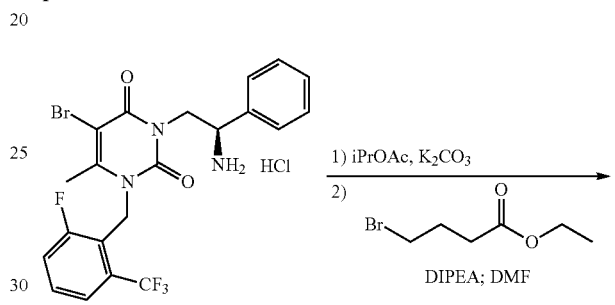

N-4

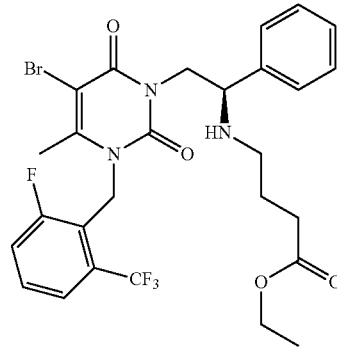

N-3

5 g of intermediate N-4 are suspended in 23.5 mL of isopropyl acetate in a round-bottom flask.

The solution of potassium carbonate (8.68 g) in water (33.5 mL) is added and kept under vigorous agitation at 25° C. for 2 hours.

The phases are separated, the organic phase is washed twice with water and 5 mL of N,N-dimethylformamide are added.

The isopropyl acetate is removed at reduced pressure at 45° C. and 2.0 mL of ethyl 4-bromo-butanoate and 2.9 mL of N,N-diisopropylethylamine are added to the solution. The solution is kept under agitation at 35° C. for 40 hours.

At the end of the reaction (the reaction is controlled using HPLC analysis) it is cooled to 25° C. and 25 mL of water and 25 mL of isopropyl acetate are added.

The phases are separated, the organic phase is washed in sequence with water, with a NaCl aqueous solution, with 1M HCl acidic aqueous solution, with 8% NaHCO₃ basic aqueous solution and finally with water.

The organic phase is concentrated at reduced pressure at 45° C. removing at least 90% of the solvent obtaining a yellow oil that is used as such in the reaction of the following example.

EXAMPLE 11

This example relates to the performance of step d) of the process of the invention in which the protic acid is phosphoric acid.

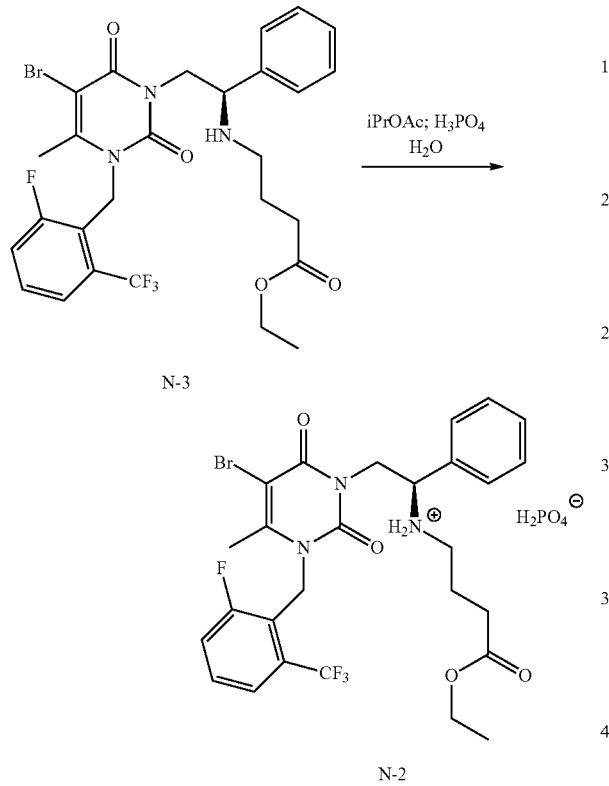

The composition of the sample was determined using elementary analysis for carbon, hydrogen and nitrogen, and with ionic chromatography for phosphates, providing the following results: Carbon=43.62%; Hydrogen=4.27%; Nitrogen=5.60%; Phosphates=15.78% in accordance with the proposed structure (dihydrogen phosphate salt of intermediate N-3).

EXAMPLE 12

This example relates to step e) of the process of the invention in which the intermediate N-2 is salified with phosphoric acid.

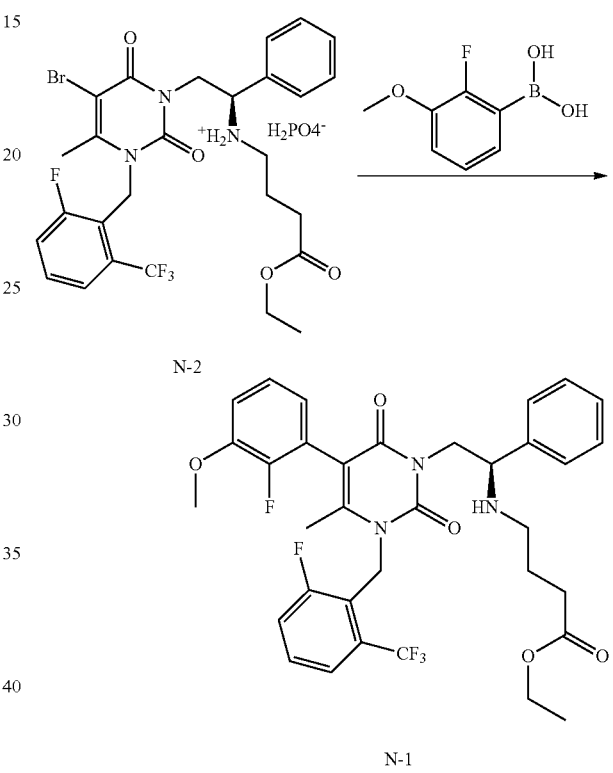

The intermediate N-3 (250 mL) obtained as described in Example 10 is dissolved in 1.1 L of isopropyl acetate.

The solution is treated with a solution of 85% orthophosphoric acid (57 g) in water (614 mL).

The phases are separated and the organic phase is re-extracted with a solution of 85% orthophosphoric acid (23.4 g) in water (145 mL).

The aqueous phase, containing the product, is kept under agitation at 25° C. until the precipitation of a white solid that is filtered and washed with water on the filter.

It is dried at reduced pressure at 50° C. until reaching a constant weight.

231 g of intermediate N-2 are obtained (white solid, titre HPLC 98.1%) which is used as such for the subsequent step without any further purifications.

$^1$H-NMR (400 MHz, CDCl$_3$): 7.67-7.49 (m, 3H); 7.30-7.24 (m, 5H); 5.33 (s, 2H); 4.11-4.05 (m, 3H); 4.00 (dd, 2H, J=7.5 Hz); 2.52-2.50 (m, 3H); 2.37 (t, 2H, J=6.9 Hz); 2.23 (t, 2H, J=7.3 Hz); 1.61-1.57 (m, 2H); 1.13 (t, 3H, J=7.2 Hz).

Figure 4:
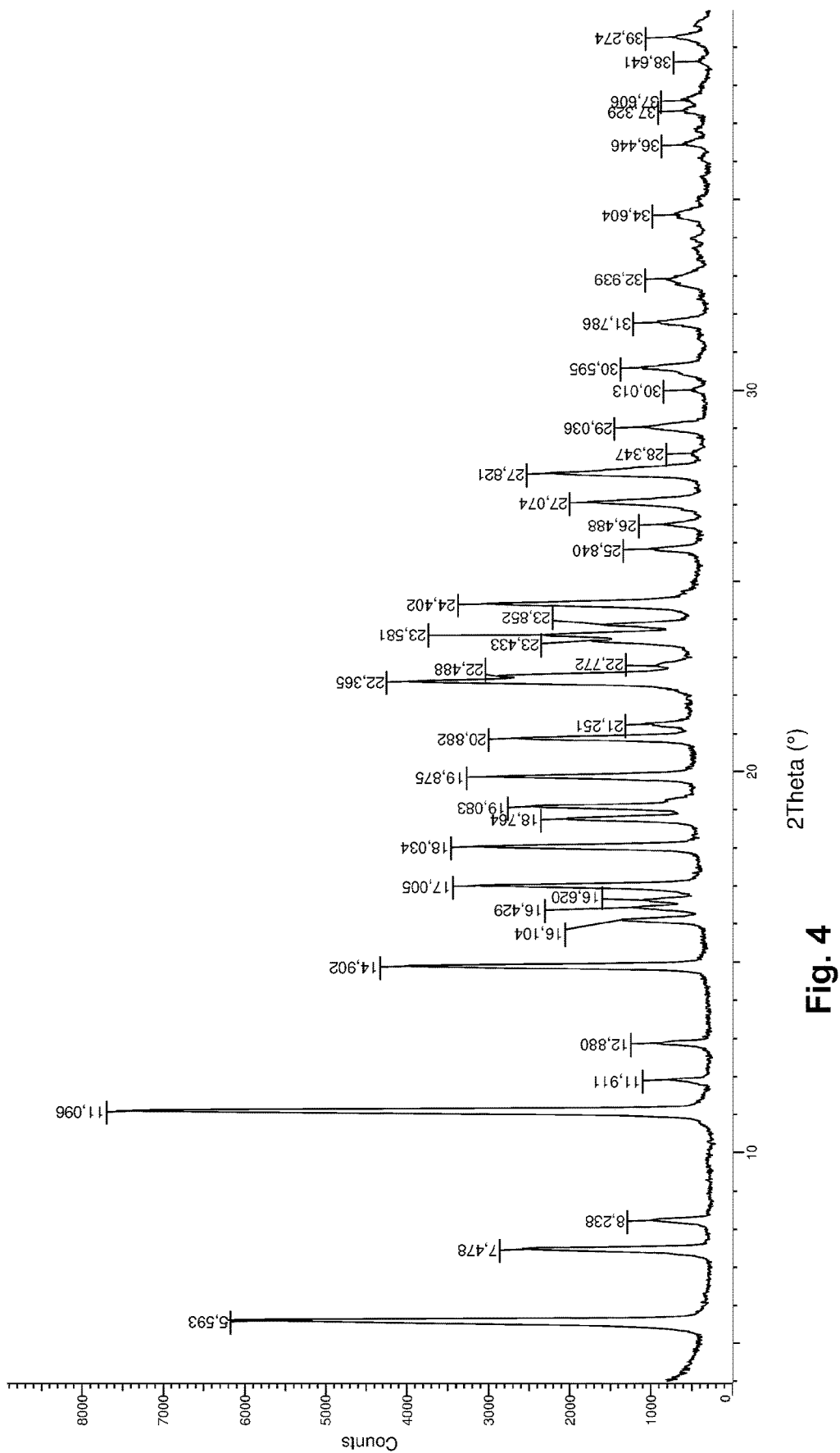
FIG. 4 shows the DRX diffraction spectrum of the intermediate N-2 that can be obtained following the experimental procedure of Example 11.
Figure 5:
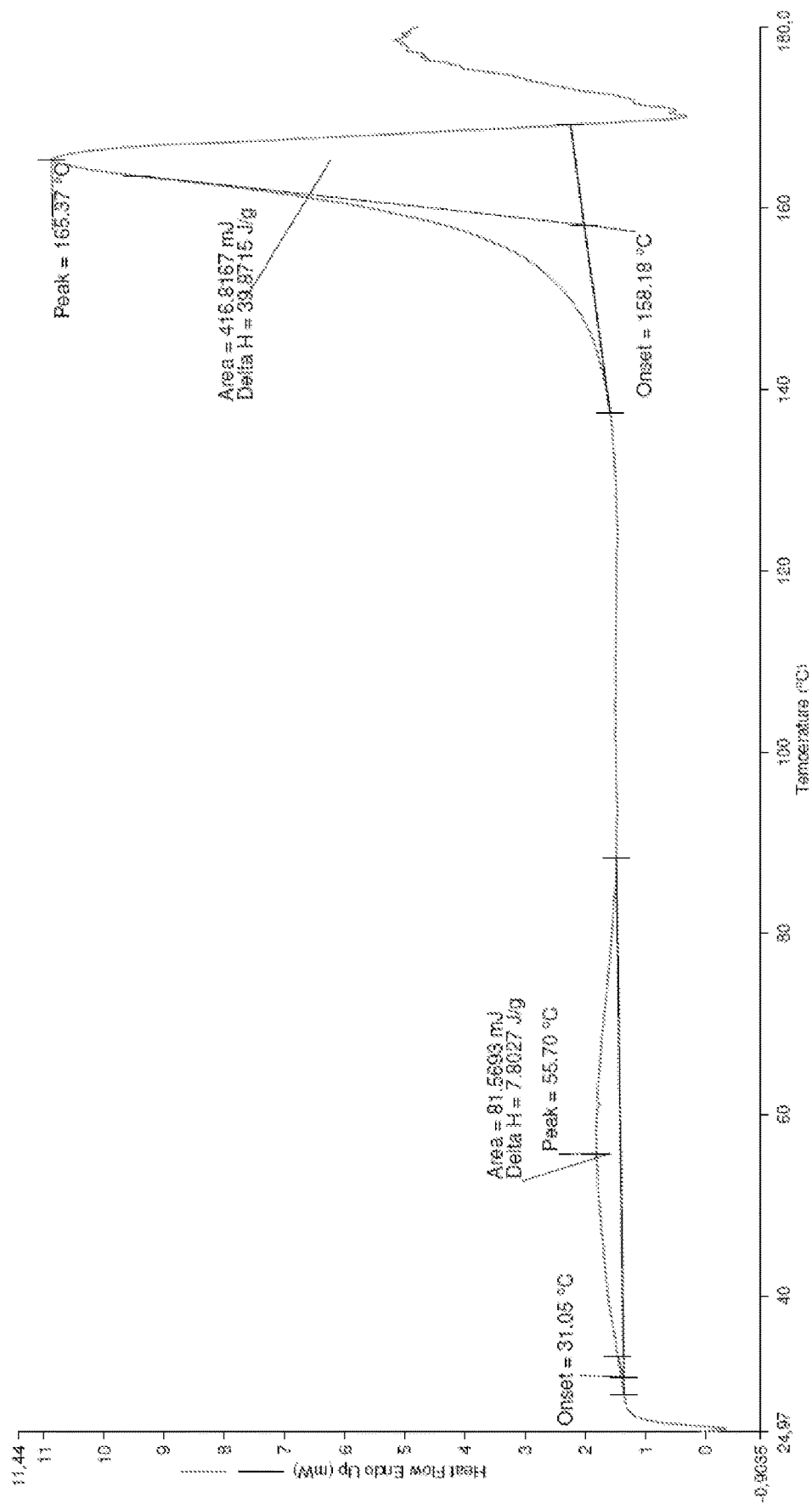
FIG. 5 shows the DSC thermogram of the intermediate N-2 that can be obtained following the experimental procedure of Example 11.
Figure 6:
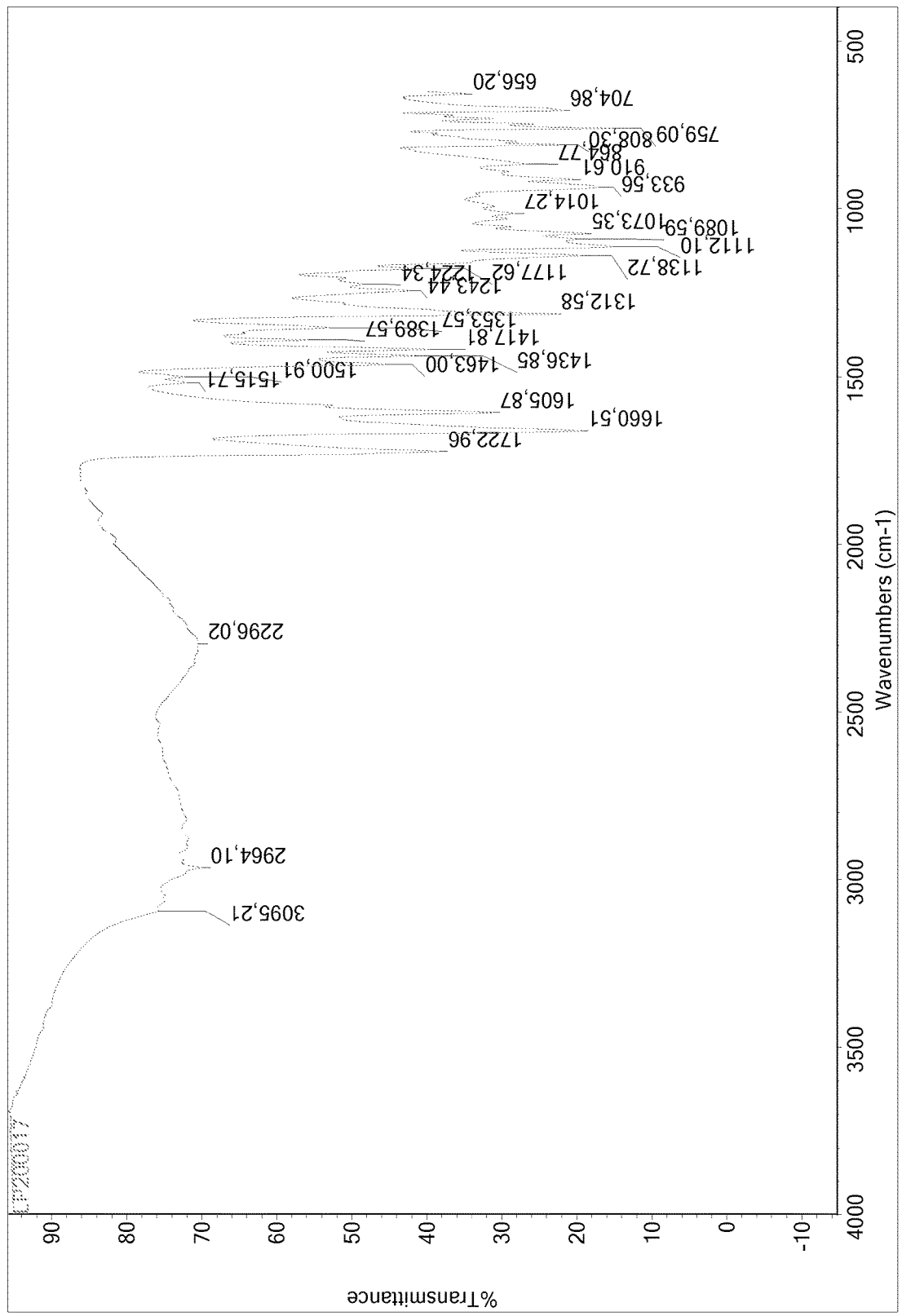
FIG. 6 shows the FT-IR spectrum of the intermediate N-2 that can be obtained following the experimental procedure of Example 11.

FIGS. 4, 5 and 6 reproduce, respectively, the DRX diffraction spectrum, the DSC thermogram and the FT-IR spectrum, obtained with the instruments and methods described above, of the intermediate N-2 produced in this example.

In a round-bottom flask under nitrogen, the intermediate N-2 obtained following the procedure of Example 11 (200 g), 2-fluoro-3-methoxyphenylboronic acid (138 g) and tri-t-butyl phosphonium tetrafluoroborate (18 g) and acetone (2250 mL) are loaded.

After degassing the suspension with nitrogen, the reaction mixture is cooled to 5° C. to which is added a solution of potassium hydroxide (88 g) in water (880 mL) previously degassed with nitrogen, keeping the temperature below 15° C.

It is heated to 45° C., palladium acetate (7 g) is added and it is kept under agitation for 2 hours under a nitrogen atmosphere (HPLC control, intermediate N-2 not detectable).

It is cooled to 25° C.

Water (1000 mL), isopropyl acetate (1000 mL) and dicalite are added.

The system is filtered, the phases are separated washing the organic phase with water.

After concentrating the organic phase at reduced pressure at 40° C. until a small volume it is poured onto an acidic solution obtained by mixing 85% orthophosphoric acid (117 g) with water (1250 mL).

The two-phase system obtained is kept under agitation at 25° C. for 30 minutes.

The phases are separated: the product is in the aqueous phase, which is washed with isopropyl acetate.

The phases are separated and the aqueous phase (which contains the product) is dripped onto a basic solution obtained with potassium carbonate (271 g) and water (345 mL), keeping the temperature at 25-30° C.

Isopropyl acetate (2350 mL) is added and the two-phase system is agitated at 25° C. for 20 minutes.

The phases are separated, the organic phase is washed with water, and is concentrated at reduced pressure at 45° C. until oil (HPLC purity =93.6%) which is dissolved with dichloromethane (145 ml).

A portion of the solution (150 mL) is placed in agitation with 70 g of silica gel and 9 g of decolorizing carbon for 2 hours.

The suspension is filtered by washing the residue with dichloromethane and the organic solution is further filtered on a membrane filter obtaining, after evaporation of the solvent, the intermediate N-1 (70 g of oil, HPLC purity=98.1%).

Such intermediate can be used as such for step f) of the invention.

The remaining part of solution containing the intermediate N-1 in dichloromethane is filtered on silica gel in the same way as described in Example 5 and used in the subsequent step f) of the invention.

The invention claimed is:
1. A process for the synthesis of the sodium salt of Elagolix, which comprises the following steps:
 a) reaction of the compound 5-bromo-1-[2-fluoro-6-(trifluoromethyl)benzyl]-6-methylpyrimidine-2,4(1H,3H)-dione (N-6) with D-Boc-phenylglycinol to obtain the intermediate 5-bromo-1-[2-fluoro-6-(trifluoromethyl)benzyl]-6-methyl-3-[2(R)-tert-butoxycarbonylamino-2-phenylethyl]-pyrimidine-2,4(1H,3H)-dione (N-5):

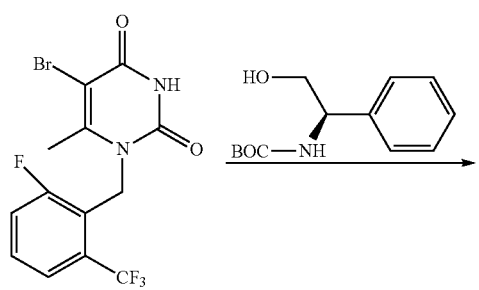

N-6 b) treatment of the intermediate N-5 with hydrochloric acid in a solvent selected among ethanol, methanol, isopropanol, acetone, methyl isobutyl ketone (MIBK), ethyl acetate, isopropyl acetate or a mixture thereof, to obtain the intermediate 5-bromo-1-[2-fluoro-6-(trifluoromethyl)benzyl]-6-methyl-3-[2(R)-amino-2-phenylethyl]-pyrimidine-2,4(1H,3H)-dione hydrochloride (N-4):

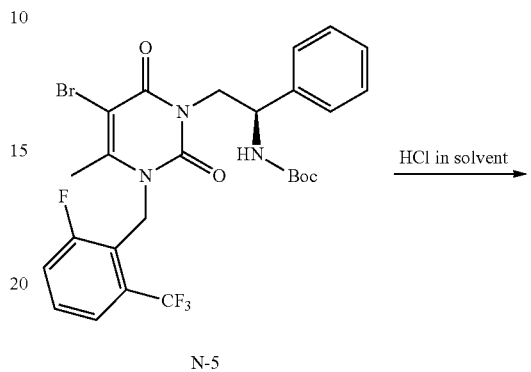

N-5

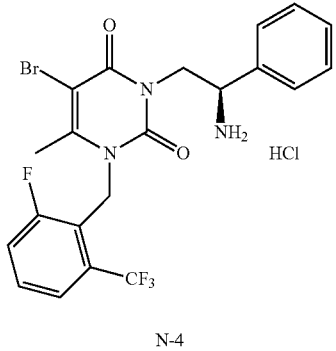

N-4 c) treatment with bases of the intermediate N-4 and reaction with ethyl 4-bromobutanoate at a temperature between 30 and 55° C. to obtain the intermediate 3-[2(R) -{ethoxycarbonylpropylamino}-2-phenylethyl]-5-bromo-1-[2-fluoro-6-(trifluoromethyl)benzyl]-6-methyl-pyrimidine-2,4(1H,3H)-dione (N-3):

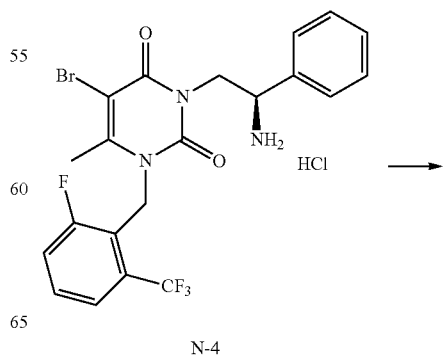

N-4

-continued

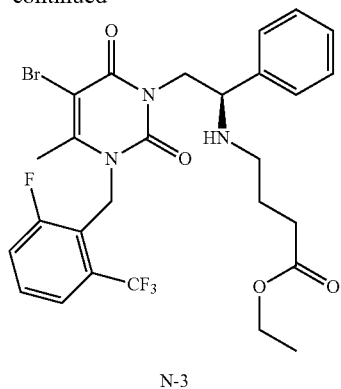

N-3 d) treatment of the intermediate N-3 with a protic acid (AH) to obtain the corresponding salt (intermediate N-2):

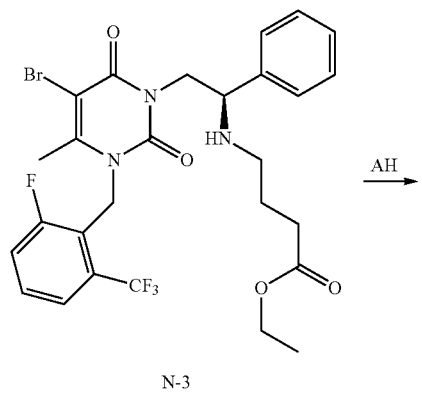

N-3

↓ AH

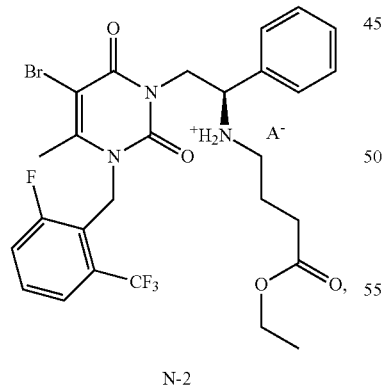

N-2 wherein A⁻ is a conjugate base of the protic acid;

e) reaction of the intermediate N-2 with 2-fluoro-3-methoxyphenylboronic acid to obtain the intermediate 3-[2(R)-{ethoxycarbonylpropyl-amino   }-2-phenyl-ethyl]-5-(2-fluoro-3-methoxyphenyl)-1[2-fluoro-6-(tri-fluoromethyl)benzyl]-6-methyl-pyrimidine  -2,4(1H, 3H)-dione (N-1):

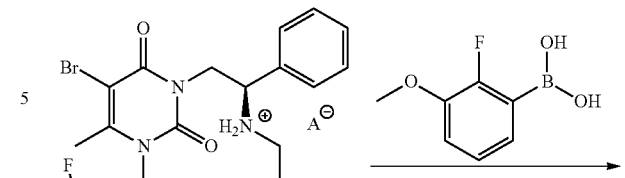

N-2

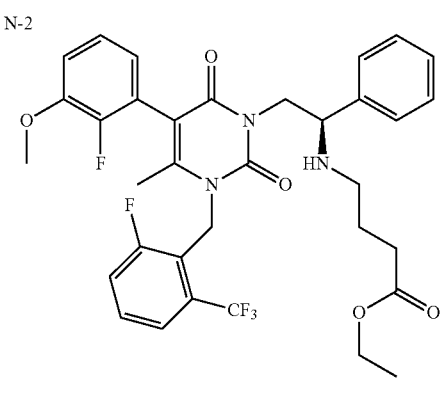

N-1 f) formation of the sodium salt of Elagolix by reaction of the intermediate N-1 with sodium hydroxide:

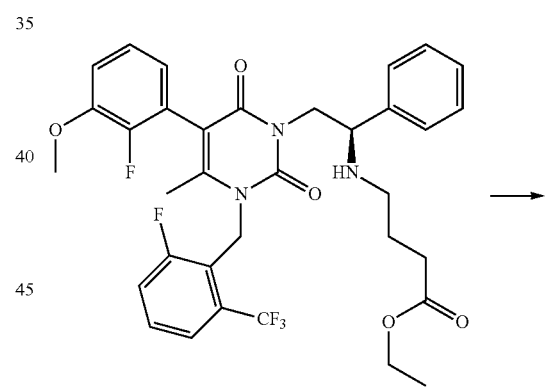

N-1

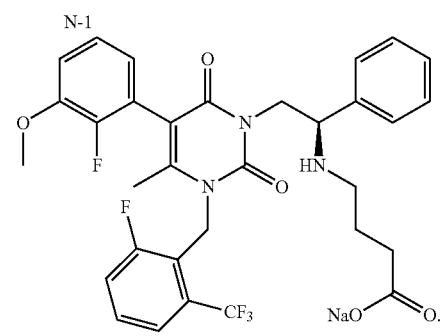

ELAGOLIX SODIUM

2. The process according to claim 1, wherein the intermediate N-5 obtained in step a) is purified by treating the crude product with an organic ester selected from ethyl acetate (AcOEt), butyl acetate (BuOAc) and isopropyl acetate (iPrOAc) and subsequent removal, by filtration at a temperature between 0 and 25° C., of the by-products of step a).

3. The process according to claim 1 wherein step b) is carried out by adding, to a solution of intermediate N-5 in an organic solvent selected from ethanol, methanol, isopropanol, acetone, methyl isobutyl ketone, ethyl acetate, isopropyl acetate and mixtures thereof, hydrochloric acid in the form of gas or dissolved in said organic solvent, at a temperature between 5 and 35° C.

4. The process according to claim 1, in which step c) is performed with a sequence of two operations, in which the first, c.1, consists in suspending intermediate N-4 in an organic ester selected from ethyl acetate (AcOEt), butyl acetate (ButOAc) and isopropyl acetate (iPrOAc) and treating it with an inorganic base; and the second, c.2, consists in reacting the amino function released in operation c.1 with the compound ethyl 4-bromo-butanoate at a temperature between 35 and 55° C.

5. The process according to claim 1, in which step d) is performed with a sequence of two operations, in which the first, d.1, consists in preparing a solution of the intermediate N-3 in an organic solvent selected from ethanol, methanol, isopropanol, acetone, methyl isobutyl ketone, ethyl acetate, isopropyl acetate, butyl acetate and mixtures thereof, and adding to said solution a protic acid as a gas or dissolved in the solvent, at a temperature between 10 and 35° C.; and the second, d.2, consists in isolating the intermediate N-2 obtained by filtration after precipitation of the salt from the organic phase acidified by the addition of an antisolvent or by filtration after precipitation of the salt from the corresponding aqueous phase.

6. The process according to claim 1, wherein in step d) hydrochloric acid or phosphoric acid are used as the protic acid.

7. 3-[2(R)-{Ethoxycarbonylpropylamino}-2-phenylethyl]-5-bromo-1-[2-fluoro-6-(trifluoromethyl)benzyl]-6-methyl-pyrimidine-2,4(1H,3H)-dione (intermediate N-3):

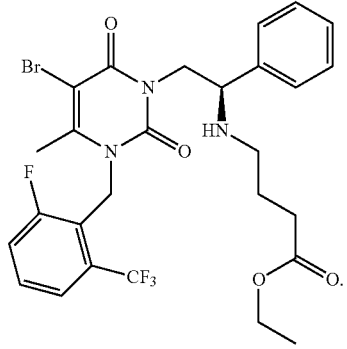

8. Salt of 3-[2(R)-{ethoxycarbonylpropyl-amino}-2-phenylethyl]-5-bromo-1-[2-fluoro-6-(trifluoromethyl)-benzyl]-6-methyl -pyrimidine-2,4(1H,3H)-dione (intermediate N-2)

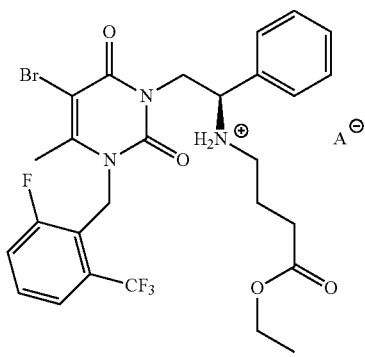

wherein A⁻ is a conjugate base of a protic acid.

9. The salt according to claim 8, wherein said protic acid is selected from hydrochloric acid, sulfuric acid, phosphoric acid, hydrobromic acid, p-toluenesulfonic acid and trifluoroacetic acid.

10. The salt according to claim 9, wherein said protic acid is selected from hydrochloric acid and phosphoric acid.

11. The salt according to claim 8, wherein the conjugate base A⁻ is phosphate ($PO_4^{3-}$), hydrogen phosphate ($HPO_4^{2-}$), dihydrogen phosphate ($H_2PO_4^-$) and mixtures thereof.

12. A process for the synthesis of the sodium salt of Elagolix, which comprises the following steps:
providing a salt of 3-[2(R)-{ethoxycarbonylpropyl-amino}-2-phenylethyl]-5-bromo-1-[2-fluoro-6-(trifluoromethyl)-benzyl]-6-methyl-pyrimidine-2,4(1H, 3H)-dione (intermediate N-2)

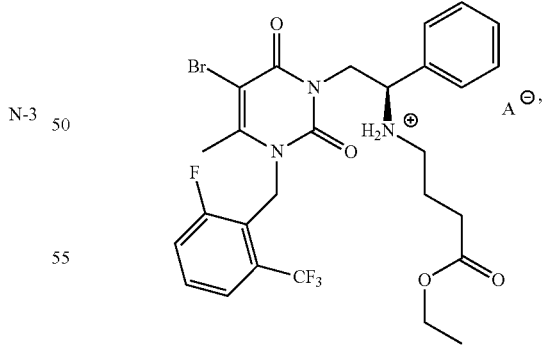

wherein A⁻ is a conjugate base of a protic acid;
reacting intermediate N-2 with 2-fluoro-3-methoxyphenylboronic acid to obtain the intermediate 3-[2(R)-{ethoxycarbonylpropyl-amino}-2-phenylethyl]-5-(2-fluoro-3-methoxyphenyl)-1-[2-fluoro-6-(trifluoromethyl)benzyl]-6-methyl -pyrimidine-2,4(1H, 3H)-dione (N-1):

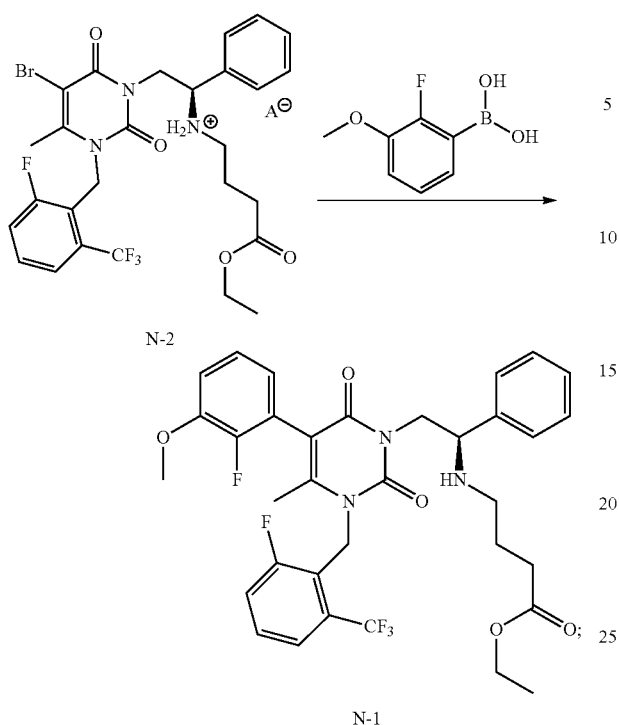

N-2

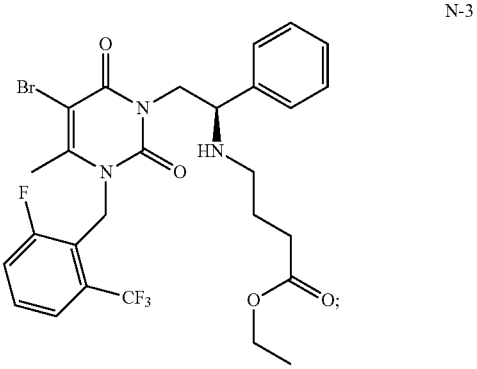 [SMILES: CCOC(=O)CCCN[C@@H](Cn1c(=O)c(Br)c(C)n(Cc2c(F)cccc2C(F)(F)F)c1=O)c1ccccc1]

and
forming the sodium salt of Elagolix by reaction of the intermediate N-1 with sodium hydroxide:

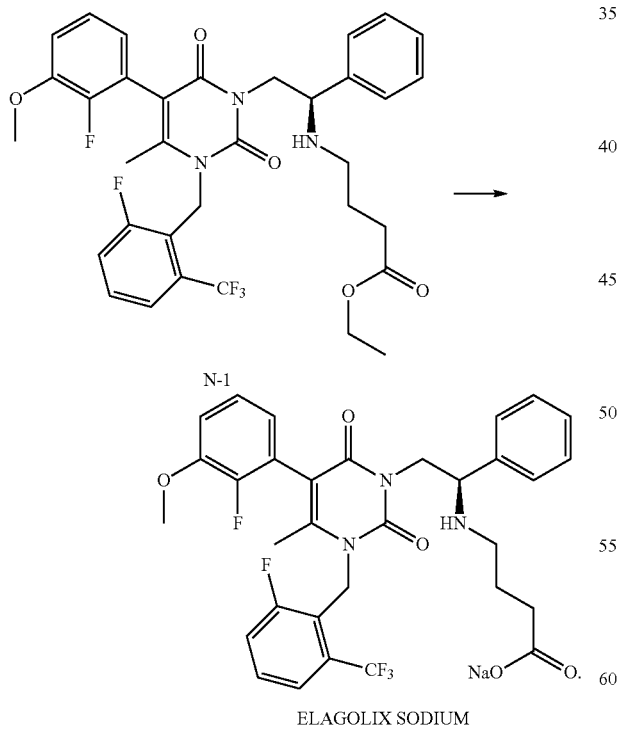

ELAGOLIX SODIUM

13. The process of claim 12, further comprising:

providing intermediate 3-[2(R)-{ethoxycarbonylpropylamino}-2-phenylethyl]-5-bromo -1-[2-fluoro-6-(trifluoromethyl)benzyl]-6-methyl-pyrimidine-2,4(1H, 3H)-dione (N-3)

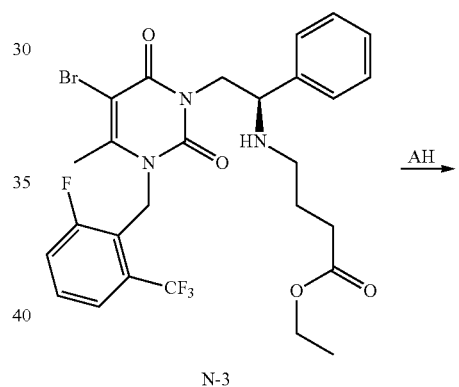

treating intermediate N-3 with a protic acid (AH) to obtain the corresponding salt intermediate N-2:

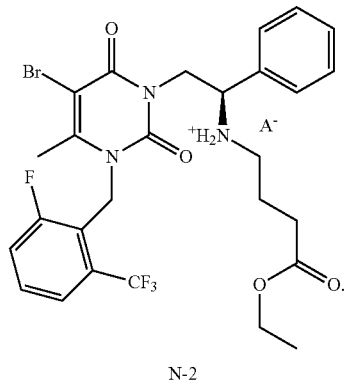

* * * * *